United States Patent
Gañán-Calvo

(12) 
(10) Patent No.: US 6,248,378 B1
(45) Date of Patent: *Jun. 19, 2001

(54) ENHANCED FOOD PRODUCTS

(75) Inventor: Alfonso Gañán-Calvo, Seville (ES)

(73) Assignee: Universidad de Sevilla, Seville (ES)

( * ) Notice: Subject to any disclaimer, the term of this patent is extended or adjusted under 35 U.S.C. 154(b) by 0 days.

This patent is subject to a terminal disclaimer.

(21) Appl. No.: 09/468,707

(22) Filed: Dec. 21, 1999

Related U.S. Application Data

(63) Continuation-in-part of application No. PCT/IB98/02053, filed on Dec. 16, 1998.

(51) Int. Cl.$^7$ .................................................. A23P 1/04
(52) U.S. Cl. ........................ 426/89; 426/302; 426/442; 426/474; 424/439; 424/489; 424/490
(58) Field of Search ........................... 426/89, 302, 281, 426/442, 474; 424/439, 489, 490

(56) References Cited

U.S. PATENT DOCUMENTS

| | | | |
|---|---|---|---|
| 4,722,847 | 2/1988 | Heckert | 426/74 |
| 5,453,383 | * 9/1995 | Roufs et al. | 426/302 |
| 5,876,775 | * 3/1999 | Behnke et al. | 426/302 |
| 6,116,516 | * 9/2000 | Ganan-Calvo | 239/8 |
| 6,119,953 | * 9/2000 | Ganan-Calvo et al. | 239/8 |

FOREIGN PATENT DOCUMENTS

| | | | |
|---|---|---|---|
| 97/43048 | * | 11/1997 | (WO) |
| 99/30812 | * | 6/1999 | (WO) |
| 99/30831 | * | 6/1999 | (WO) |
| 99/30832 | * | 6/1999 | (WO) |
| 99/30833 | * | 6/1999 | (WO) |
| 99/30834 | * | 6/1999 | (WO) |
| 99/30835 | * | 6/1999 | (WO) |
| 99/31019 | * | 6/1999 | (WO) |

OTHER PUBLICATIONS

Hollingsworth, "Mainstreaming Healthy Foods," *Food Technology*, 51:55–58 (1997).
Giese et al., "Ethical Marketing of Functional Foods," *Food Technology*, 51:58–61 (1997).

* cited by examiner

*Primary Examiner*—Milton Cano
(74) *Attorney, Agent, or Firm*—Karl Bozicevic; Dianna L. DeVore; Bozicevic, Field & Francis LLP

(57) ABSTRACT

The invention is directed to production of particles for introduction into food using a stable microjet and a monodisperse aerosol formed when the microjet dissociates. A variety of devices and methods are disclosed which allow for the formation of a stream of a first fluid (e.g. a liquid) characterized by forming a stable capillary microjet over a portion of the stream wherein the microjet portion of the stream is formed by a second fluid (e.g. a gas).

10 Claims, 4 Drawing Sheets

ENHANCED FOOD PRODUCTS

CROSS REFERENCES

This application is a Continuation in Part of earlier filed PCT Application PCT/IB98/02053 filed Dec. 16, 1998.

FIELD OF THE INVENTION

The invention relates generally to the field of small particle formation and more specifically to improvement of foods by the introduction of particles which are very small and uniform in size.

BACKGROUND OF THE INVENTION

Advances in food technology are improving the foods that are available to consumers and promoting good health both through basic nutrition and through enhanced benefits of food products. Foods are being improved through the reduction or removal of certain components in a food, increasing the amount of certain components normally found in the food, or adding components to a food which are not normally found in the food. Products in which the amount of a component or ingredient naturally or normally present is increased or reduced include breakfast cereals with added bran or dairy products with reduced fat. Products with components or ingredients not normally present to any significant extent include fruit juice with added fiber, bread with added folic acid, and margarine spreads containing fish oils or olive oil.

Foods with components not normally present in those foods has become increasingly popular with the introduction of "functional foods". A functional food is any non-toxic food or food ingredient that has been altered to provide medical or health benefits, including the prevention and treatment of disease. Functional foods are similar in appearance to conventional foods that are consumed as part of a “normal” diet, but have additives that demonstrate physiological benefits beyond their nutritive content. These products include genetically engineered “designer” foods, herbal products, and processed products, such as cereals, soups and beverages. Functional food product development reflects a major shift in attitude and an application of current knowledge about diet and health from ‘removing the bad’ (for example, fat, cholesterol and salt) to ‘adding or enhancing the good’ (such as calcium, fiber, antioxidants and botanicals). This has, in turn, paralleled consumer interest in healthy eating. Hollingsworth, P., *Food Technol.,* 1997, 51, 55–8; Giese, J., & Katz, F., *Food Technol.,* 1997, 51, 58–61. Consumers and their demand for an improved quality of life are bringing worldwide growth to the functional food industry.

Currently, a number of functional foods are being offered to consumers, including fortified breads, cereals, juices, and the like. For example, juice containing the patented calcium source FruitCal™ (calcium citrate malate), U.S. Pat. No. 4,722,8470, which is more readily absorbable in juice (>35%) than calcium from milk or calcium carbonate supplements, is widely marketed. These fortified juices provide protection against osteoporosis and promote healthy teeth and bones. Certain functional foods are also being introduced to prevent, treat or ameliorate physiological conditions such as cardiovascular disease, hypercholesterolemia, and even menopause. For example, breakfast cereals with the compound PHYTROL™ added are marketed as foods to control cholesterol.

The opportunity for future growth and development of new functional foods worldwide is tremendous. Overwhelming evidence supports the link between diet and optimal health, particularly the prevention of degenerative diseases of aging such as cancer, heart disease, osteoporosis, diabetes, arthritis and stroke. Given the extended life expectancy for those in developed nations and the commensurate increase in healthcare costs associated with treating chronic ageing diseases, there will be more of an emphasis in the future on a preventative rather than a prophylactic approach to healthcare. Diet will play a critical role in this new paradigm.

There is thus a new demand for new methods of improving foods by adding components to these foods to improve nutrient content, reduce the amount or percentage of unwanted components (e.g., fats) or provide functional components that increase the physiological response beyond that of conventional food products.

SUMMARY OF THE INVENTION

The invention is directed to production of particles for introduction into food using a stable microjet and a monodisperse aerosol of liquid particles formed when the microjet dissociates. A variety of devices and methods are disclosed which allow for the formation of a stream of a first fluid (e.g. a liquid) characterized by forming a stable capillary microjet over a portion of the stream wherein the microjet portion of the stream is formed by a second fluid (e.g. a gas). The second fluid is preferably in a different state from the first fluid—liquid-gas or gas-liquid combinations. However, the first and second fluids may be two different fluids immiscible in each other.

In preferred embodiments the first fluid is a liquid which forms a food or food additive and the second fluid is a gas which is non-toxic, e.g. air or nitrogen. In a particularly preferred embodiment the first fluid comprised of material which it would be desirable to have in but which can not be added to food for some reason, e.g. bad taste or reacts with the food. The first fluid is surrounded by a second fluid which is also a liquid, but which can coat and encapsulate the first fluid. A third fluid surrounds the second fluid and the third fluid is preferably a gas which focuses the liquid stream to a microjet. The jet will break up into particles where the first fluid (liquid food) is coated with the second fluid (liquid carrier coating). The coating provided by the second fluid keeps the bad taste or reactive effects of the first fluid from having its undesirable effects.

Many preferred embodiments provide a spheric food particle coated with a layer of another material which is non-toxic (e.g. a polymer which is degraded in the G.I.) and may or may not be a food product. The coating material may be a polymer which is maintained in a flowable liquid form until it coats the internal food particle after which the polymer coating is “cured,” polymerized or made non-flowable in some manner, e.g. by exposure to certain light energy, curing agent or a decreased temperature.

Although many specific embodiments described here relate specifically to foods those embodiments are applicable to drugs and nutriceuticals and other materials. Further, the drug embodiments described are applicable to foods, nutriceuticals and other materials.

The stable capillary microjet comprises a diameter $d_j$ at a given point A in the stream characterized by the formula:

$$d_j \cong \left(\frac{8\rho_l}{\Pi^2 \Delta P_g}\right)^{\frac{1}{4}} Q^{\frac{1}{2}}$$

wherein $d_j$ is the diameter of the stable microjet, indicates approximately equally to where an acceptable margin of error is ±10%, $\rho_l$ is the density of the liquid and $\Delta P_g$ is change in gas pressure of gas surrounding the stream from the feeding point to the point A, and wherein Q is the flow rate of the focused liquid.

The microjet can have a diameter in the range of from about 1 micron to about 1 mm and a length in the range of from 1 micron to 50 mm. The stable jet is maintained, at least in part, by tangential viscous stresses exerted by the gas on the surface of the jet in an axial direction of the jet. The jet is further characterized by a slightly parabolic axial velocity profile and still further characterized by a Weber number (We) which is greater than 1 with the Weber number being defined by the formula:

$$We = \frac{\rho_g V_g^2 d}{\gamma}$$

wherein the $\rho_g$ is the density of the gas, d is the diameter of the stable microjet, $\gamma$ is the liquid-gas surface tension, and $V^2_g$ is the velocity of the gas squared.

Although the Weber number is greater than 1 when a stable microjet is obtained the Weber number should be less than 40 to obtain a desired monodisperse aerosol. Thus, desired results are obtained within the parameters of $1 \leq We \leq 40$. Monodisperse aerosols of the invention have a high degree of uniformity in particle size. The particles are characterized by having the same diameter with a deviation in diameter from one particle to another in a range of about ±2% or less to about ±30%, preferably about ±3% or less to about ±10% and most preferably ±3% or less. The particles in an aerosol will have consistency in size but may be produced to have a size in a range of about 0.1 micron to about 100 microns.

An object of the invention is to provide a stream of a first fluid (e.g. a liquid) which stream is characterized by forming a stable capillary microjet over a portion of the stream wherein this stable capillary microjet portion of the stream is formed by a second fluid (e.g. a gas) moving at a velocity greater than that of the first fluid.

Another object of the invention is to provide a monodisperse aerosol of liquid particles in air wherein the particles are characterized by having the same diameter with a deviation in diameter from one particle to another in a range of from about ±3% to about ±30% wherein the particles are produced as a result of a break up of the stable capillary microjet. These particles may be dessicated following dispersion, and then added to food, or may be added to the foods in liquid form.

An advantage of the invention is that the microjet of liquid flows through an opening surrounded by a focusing funnel of gas so that liquid does not touch the peripheral area of the opening and therefor does not deposit on the opening and cause clogging.

Another advantage of the invention is that the particles formed are highly uniform in size and are created with a relatively small amount of energy.

A feature of the invention is that various parameters including the viscosities and velocities of the fluids can be chosen with consideration to other adjusted parameters to obtain a supercritical flow of liquid which results in the formation of the stable microjet.

Another feature of the invention is the production of micronutrients, which are nutrients produced in a precise size range to increase the absorption and release of these nutrients in the bloodstream.

Another feature of the invention is the ability to coat particles or form hollow spheres, thus maintaining the surface area of a substance while decreasing the overall amount of the substance (e.g., a fiber particle coated with oil or a hollow sphere composed on an antimicrobial). This can also allow introduction of components that are generally incompatible with a food, such as introduction of lactase in milk, by coating the component.

Yet another feature of the invention is the use production of time-release components that will allow controlled delivery of the contents of the particle, e.g., carbohydrates particles coated to allow a systematic release over a twelve hour period.

These and other aspects, objects, features and advantages will become apparent to those skilled in the art upon reading this disclosure in combination with the figures provided.

BRIEF DESCRIPTION OF THE DRAWINGS

FIG. 3a illustrates a cross-sectional side view of the planar feeding source and the interaction of the fluids. FIG. 3b show a frontal view of the openings in the pressure chamber, with the multiple openings through which the atomizate exits the device. FIG. 3c illustrates the channels that are optionally formed within the planar feeding member. The channels are aligned with the openings in the pressure chamber.

DETAILED DESCRIPTION OF PREFERRED EMBODIMENTS

Figure 1A:
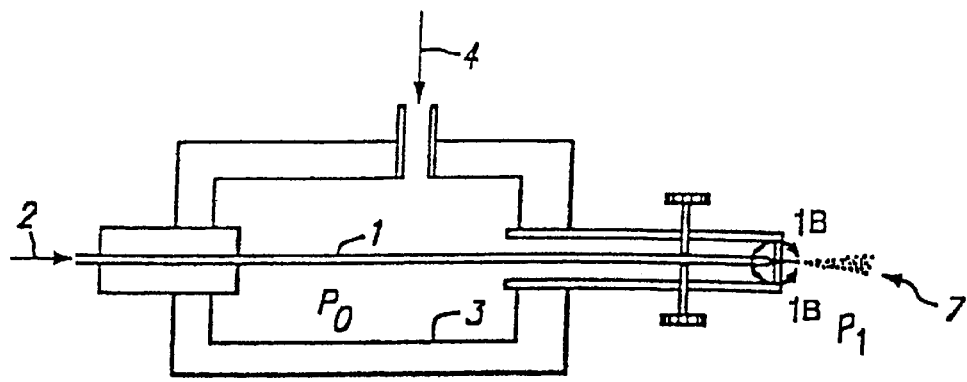
FIG. 1 is a schematic view showing the basic components of one embodiment of the invention with a cylindrical feeding needle as a source of formulation.

Before the present aerosol device and method are described, it is to be understood that this invention is not limited to the particular components and steps described, as such may, of course, vary. It is also to be understood that the terminology used herein is for the purpose of describing particular embodiments only, and is not intended to be limiting, since the scope of the present invention will be limited only by the appended claims.

It must be noted that as used herein and in the appended claims, the singular forms "a", "and," and "the" include plural referents unless the context clearly dictates otherwise. Thus, for example, reference to "a particle" includes a plurality of particles and reference to "a fluid" includes reference to a mixture of fluids, and equivalents thereof known to those skilled in the art and so forth.

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, the preferred methods and materials are now described. All publications mentioned herein are incorporated herein by reference to disclose and describe the methods and/or materials in connection with which the publications are cited.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The terms "particles", "atomized particles" and "atomized particles of formulation" are used interchangeably herein and shall mean particles of fluid formulations (preferably liquid food) that have been atomized using the device and method of the invention. The particles are generally spherical, and may be solid, coated, or hollow spheres.

The term "formulation" as used herein refers to any matter which is desired to be atomized. A formulation may contain a single component to be added to the food, or may contain multiple components. The term is also intended to encompass excipients, cariers, and the like, including compounds to which components are conjugated, as are described in the following sections.

The terms "air", "particle free air" and the like, are used interchangeably herein to describe a volume of air which is substantially free of other material and, in particular, free of particles intentionally added such as particles of formulation. The term means that the air does not include particles of formulation which have been intentionally added but is not intended to imply that the normal surrounding air has been filtered or treated to remove all particles although filtering can take place. Air is the preferred gas to use with drug delivery it being noted that other gas, e.g., $CO_2$ can be used.

The term "food" as used herein means (1) articles used for food (consumed by mouth for nutrition) or drink for man or other animals, (2) chewing gum, and (3) articles used for components of any other such food article. Food includes articles used by people in the ordinary way most people use food, i.e. for taste, aroma and/or nutritive value. The term "food" as used herein also is intended to cover food additives (e.g. condiments) and specialized foods such as infant formula.

The term "food additive" as used herein means any substance the intended use of which results or may reasonably be expected to result, directly or indirectly, in its becoming a component or otherwise affecting the characteristics of any food, including any substance intended for use in producing, manufacturing, packing, processing, preparing, treating, packaging, transporting, or holding food. The term as used herein does not include a pesticide chemical or a drug regulated by the Food and Drug Administration (as either a prescription or over the counter (OTC) drug) that has been added to the food. Examples of food additives include components which, by themselves are not additives such as vitamins, minerals, color additives, herbal additives (e.g., echinacea or St. John's Wort), antimicrobials, preservatives, and the like which when added to food are additives.

The term "color additive" as used herein includes a dye, pigment, or other substance that when added or applied to a food is capable of imparting color thereto.

The term "infant formula" as used herein refers to a food which purports to be or is represented for special dietary use solely as a food for infants by reason of its simulation of human milk or its suitability as a complete or partial substitute for human milk.

The term "improved food" as used herein refers to a food product that is improved over a conventional food product by virtue of the addition of more of a component already present in the conventional counterpart, by reduction of a component present in the conventional counterpart, or by the addition of a component not usually found in the conventional counterpart. As used, the term encompasses "functional foods", but also includes food such as breads with added carbohydrates, cereals with added vitamin and/or minerals, and foods in which undesirable components are reduced by the addition of other, more desirable components, e.g., the replacement of fat with a fat substitute.

The term "functional food" as used herein refers to designed food with functional additives that effectively combine ingredients not usually found together in a single food source. Functional foods have the appearance and structure of conventional foods, but contain significant levels of biologically active components that impart health benefits or desirable physiological effects beyond basic nutrition. An example of a functional food is a food that is not normally high in fiber or protein to which either fiber or protein are added. Another example of a functional food is an infant formula with additives, such as echinacea extract, to boost immunological resistance. Yet another example of a functional food is a dairy product with a food additive, such as lactase, to combat lactose intolerance. Yet another example of a functional food is a sports drinks in which the carbohydrates are slowly released in the body so that they supply energy over a prolonged period.

The term "component" as used herein refers to any additive to a food that imparts a positive benefit to a person ingesting the food.

The term "functional component" as used herein refers to any additive to a functional food that imparts the health benefits and desirable physiological effects of the functional food. Examples of such functional components can be seen in Table 1.

TABLE 1

EXAMPLES OF FUNCTIONAL COMPONENTS

| COMPONENT | SOURCE | POTENTIAL BENEFIT |
|---|---|---|
| CAROTENOIDS | | |
| alpha-carotene | carrots | neutralize free radicals which may cause damage to cells |
| beta-carotene | various fruits, vegetables | neutralize free radicals |
| lutein | green vegetables | contribute to maintenance of healthy vision |
| lycopene | tomato & tomato products (ketchup, sauces, etc.) | may reduce the risk of prostate cancer |
| zeaxanthin | eggs, citrus, corn | contribute to maintenance of healthy vision |
| COLLAGEN HYDROLYSATE | | |
| collagen hydrolysate | gelatine | may help improve some symptoms associated with osteoarthritis |

TABLE 1-continued

EXAMPLES OF FUNCTIONAL COMPONENTS

| COMPONENT | SOURCE | POTENTIAL BENEFIT |
|---|---|---|
| DIETARY FIBER | | |
| insoluble fiber | wheat bran | may reduce the risk of breast or colon cancer |
| beta glucan | oats | reduce risk of cardiovascular disease (CVD) |
| soluble fiber | psyllium | reduce risk of CVD |
| FATTY ACIDS | | |
| omega-3 fatty acids-DHA/EPA | tuna; fish and marine oils | may reduce risk of CVD & improve mental, visual functions |
| conjugated linoleic acid (CLA) | cheese, meat products | may improve body composition, may decrease risk of certain cancers |
| FLAVONOIDS | | |
| anthocyanidins | fruits | neutralize free radicals; may reduce risk of cancer |
| catechins | tea | |
| flavanones | citrus | |
| flavones | fruits/vegetables | |
| GLUCOSINOLATES, INDOLES, ISOTHIOCYANATES | | |
| sulphoraphane | cruciferous vegetables (broccoli, kale), horseradish | neutralize free radicals, may reduce risk of cancer |
| PHENOLS | | |
| caffeic acid | fruits, vegetables, citrus | antioxidant-like activities, may reduce the risk of degenerative diseases; heart disease, eye disease |
| ferulic acid | | |
| PLANT STEROLS | | |
| stanol ester | corn, soy, wheat, wood oils | lower blood cholesterol levels by inhibiting cholesterol absorbtion |
| PREBIOTICS/PROBIOTICS | | |
| fructo-oligosaccharides (FOS) | Jerusalem artichokes, shallots, onion powder | may improve gastrointestinal health |
| lactobacillus | yogurt, other dairy | may improve gastrointestinal health |
| SAPONINS | | |
| saponins | soybeans, soy foods, protein-containing foods | may lower LDL cholesterol; contains anti-cancer enzymes |
| SOY PROTEINS PHYTOESTROGENS | | |
| ISOFLAVONES | | |
| daidzen | soybeans and soy-based foods | may reduce menopause symptoms, such as hot flashes |
| genistein | | may protect against heart disease and some cancers; lower LDL cholesterol, total cholesterol and triglycerides |
| LIGNANS | flax, rye, vegetables | |
| SULFIDES | | |
| THIOLS | | |
| diallyl sulfide | onions, garlic, olives, leeks, scallions | lower LDL cholesterol, maintain healthy immune system |
| allyl methyl trisulfide, dithiolthiones | cruciferous vegetables | |
| TANNINS | | |
| proanthocyanidins | cranberries, cranberry products, cocoa, chocolate | may improve urinary tract health may reduce risk of CVD |

The term "nutriceutical" as used herein refers to products produced from foods and/or natural sources (e.g., herbal extracts) that are sold in medicinal forms such as pills, powders and potions. Nutriceuticals impart health benefits or desirable physiological effects that are not generally associated with food.

The terms "vitamins", "minerals", "vitamin and minerals" and the like as used herein generally refer to nutritive food additives that may be found in or added to a food product. As used herein, "vitamin supplements" and "mineral supplements" are considered to be dietary supplements, and as they are separate products they do not fall under the definition of "food" per se, but rather are considered to be nutriceuticals for purposes of the present application.

The term "drug" as used herein means (1) articles recognized in the official United States Pharmacopeia, official Homeopathic Pharmacopeia of the United States, or official National Formulary, or the Physician's Desk Reference (PDR) any supplement to any of them; and (2) articles intended for use in the diagnosis, cure, mitigation, treatment, or prevention of disease in man or other animals; and (3) articles (other than food) intended to affect the structure or any function of the body of man or other animals; and (4) articles intended for use as a component of any articles specified in (1), (2) or (3).

DEVICE IN GENERAL

Different embodiments of the device used to produce particles for addition to food are shown and described herein (see FIGS. 1, 2 and 3) which could be used in producing the stable capillary microjet and/or a dispersion of particles which are substantially uniform in size. Although various embodiments are part of the invention, they are merely provided as exemplary devices which can be used to convey the essence of the invention, which is the formation of a stable capillary microjet and/or uniform dispersion of particles.

The basic device for use with the invention comprises (1) a means for supplying a first fluid and (2) a pressure chamber supplied with a second fluid which flows out of an exit opening in the pressure chamber. The exit opening of the pressure chamber is down stream of and preferably aligned with the flow path of the means for supplying the first fluid. The embodiments of FIGS. 1, 2 and 3 clearly show that there can be a variety of different means for supplying the first fluid. Other means for supplying a first fluid flow stream will occur to those skilled in the art upon reading this disclosure.

Further, other configurations for forming the pressure chamber around the means for supplying the first fluid will occur to those skilled in the art upon reading this disclosure. Such other embodiments are intended to be encompassed by the present invention provided the basic conceptual results disclosed here are obtained, i.e. a stable microjet is formed and/or a dispersion of particle highly uniform in size is formed. To simplify the description of the invention, the means for supplying a first fluid is often referred to as a cylindrical tube (see the tube 1 of FIG. 1) and the first fluid is generally a liquid, e.g. liquid food. The fluid can be any liquid or gas depending on the overall device which the invention is used within. For example, the liquid could be a liquid formulation of a food which is high in nutritional value but has an unpleasant taste and as such needs to be coated with a polymer or other material with no taste. Further, for purposes of simplicity, the second fluid is generally described herein as being a gas and that gas is often preferably air or a non-toxic gas such as nitrogen. However, the first fluid may be a gas and second fluid a liquid or both fluids may be liquid provided the first and second fluid are sufficiently different from each other (immiscible) so as to allow for the formation of a stable microjet of the first fluid moving from the supply means to a downstream exit port of the pressure chamber. Notwithstanding these different combinations of gas-liquid, liquid-gas, and liquid-liquid, the invention is generally described with a liquid formulation being expelled from the supply means and forming a stable microjet due to interaction with surrounding air flow focusing the microjet to flow out of an exit of the pressure chamber.

Formation of the microjet and its acceleration and ultimate particle formation are based on the abrupt pressure drop associated with the steep acceleration experienced by the liquid on passing through an exit orifice of the pressure chamber which holds the second fluid (i.e. the gas). On leaving the chamber the flow undergoes a large pressure difference between the liquid and the gas, which in turn produces a highly curved zone on the liquid surface near the exit port of the pressure chamber and in the formation of a cuspidal point from which a steady microjet flows, provided the amount of the liquid withdrawn through the exit port of the pressure chamber is replenished. Thus, in the same way that a glass lens or a lens of the eye focuses light to a given point, the flow of the gas surrounds and focuses the liquid into a stable microjet. The focusing effect of the surrounding flow of gas creates a stream of liquid which is substantially smaller in diameter than the diameter of the exit orifice of either the liquid pressure supply tube or the pressure chamber. This allows liquid to flow out of the pressure chamber orifice without touching the orifice, providing advantages including (1) clogging of the exit orifice is virtually eliminated, (2) contamination of flow due to contact with substances (e.g. bacteria or particulate residue) on the orifice opening is virtually eliminated, and (3) the diameter of the stream and the resulting particles are smaller than the diameter of the exit orifice of the chamber. This is particularly desirable because it is difficult to precisely engineer holes or tubes for extrusion which are very small in diameter. Further, in the absence of the focusing effect (and formation a stable microjet) flow of liquid out of an opening will result in particles which have about twice the diameter of the exit opening. An additional advantage is that the particles are not prone to agglomeration following exit from the chamber.

The description provided here generally indicates that the fluid leaves the pressure chamber through an exit orifice surrounded by the gas and thereafter enters into a gaseous surrounding environment which may be air held at normal atmospheric pressure. However, when the first fluid is a gas and the second fluid is a liquid the fluid present outside of the chamber may also be a liquid. This configuration is particularly useful when it is necessary to create very small highly uniform bubbles which are moved into a liquid surrounding exit opening of the pressure chamber. The need for the formation of very small highly uniform bubbles into a gas occurs in a variety of different industrial applications. For example, a small air bubble can be uniformly placed in a food product such as a yellow fat (e.g. butter, margarine, mayonnaise or ice cream. By making the air bubbles very small (e.g. 1–10 microns in diameter) the bubbles are not readily detectable by a person eating the food. Further, less product is used and less calories are consumed per volume of the product.

Those skilled in the art will recognize that variations on the different embodiments disclosed below will be useful in obtaining particularly preferred results. Specific embodiments of devices are now described.

EMBODIMENT OF FIG. 1

A first embodiment of the invention where the supply means is a cylindrical feeding needle supplying liquid into a pressurized chamber of gas is described below with reference to FIG. 1.

Figure 1B:
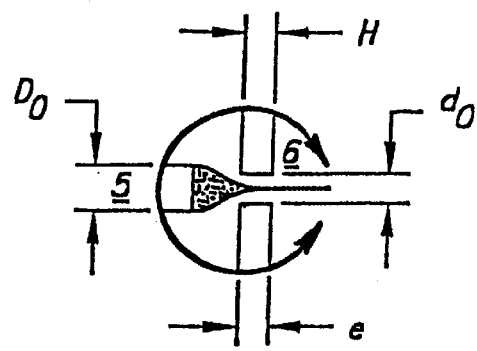

The components of the embodiment of FIG. 1 are as follows:

1. Feeding needle—also referred to generally as a fluid source and a tube.
2. End of the feeding needle used to insert the liquid to be atomized.
3. Pressure chamber.
4. Orifice used as gas inlet.
5. End of the feeding needle used to evacuate the liquid to be atomized.
6. Orifice through which withdrawal takes place.
7. Atomizate (spray)—also referred to as aerosol.

$D_O$=diameter of the feeding needle; $d_O$=diameter of the orifice through which the microjet is passed; e=axial length of the orifice through which withdrawal takes place; H=distance from the feeding needle to the microjet outlet; $P_O$=pressure inside the chamber; $P_a$=atmospheric pressure.

Although the device can be configured in a variety of designs, the different designs will all include the essential components shown in FIG. 1 or components which perform an equivalent function and obtain the desired results. Specifically, a device of the invention will be comprised of at least one source of a first fluid (e.g., a feeding needle with an opening 2) into which a first fluid such as liquid flowable formulation can be fed and an exit opening 5 from which the formulation can be expelled. The feeding needle 1, or at least its exit opening 5, is encompassed by a pressure chamber 3. The chamber 3 has inlet opening 4 which is used to feed a second fluid (e.g. a gas) into the chamber 3 and an exit opening 6 through which gas from the pressure chamber and liquid formulation from the feeding needle 3 are expelled. When the first fluid is a liquid it is expelled into gas to create an aerosol. When the first fluid is a gas it is expelled into a liquid to create bubbles.

In FIG. 1, the feeding needle and pressure chamber are configured to obtain a desired result of producing an aerosol wherein the particles are small and uniform in size or bubbles which are small and uniform in size. The particles or bubbles have a size which is in a range of 0.1 to 100 microns. The particles of any given aerosol or bubbles will all have about the same diameter with a relative standard deviation of ±10% to ±30% or more preferably ±3% to ±10%. Stating that particles of the aerosol have a particle diameter in a range of 1 to 5 microns does not mean that different particles will have different diameters and that some will have a diameter of 1 micron while others of 5 microns. The particles in a given aerosol will all (preferably about 90% or more) have the same diameter ±3% to ±30% For example, the particles of a given aerosol will have a diameter of 2 microns ±3% to ±10%.

Such a monodisperse aerosol is created using the components and configuration as described above. However, other components and configurations will occur to those skilled in the art. The object of each design will be to supply fluid so that it creates a stable capillary microjet which is accelerated and stabilized by tangential viscous stress exerted by the second fluid on the first fluid surface. The stable microjet created by the second fluid leaves the pressurized area (e.g., leaves the pressure chamber and exits the pressure chamber orifice) and splits into particles or bubbles which have the desired size and uniformity.

The parameter window used (i.e. the set of special values for the liquid properties, flow-rate used, feeding needle diameter, orifice diameter, pressure ratio, etc.) should be large enough to be compatible with virtually any liquid (dynamic viscosities in the range from $10^{-4}$ to 1 kg $m^{-1}s^{-1}$); in this way, the capillary microjet that emerges from the end of the feeding needle is absolutely stable and perturbations produced by breakage of the jet cannot travel upstream. Downstream, the microjet splits into evenly shaped drops simply by effect of capillary instability (see, for example, Rayleigh, "On the instability of jets", Proc. London Math. Soc., 4–13, 1878), similar in a manner to a laminar capillary jet falling from a half-open tap.

When the stationary, steady interface is created, the capillary jet that emerges from the end of the drop at the outlet of the feeding point is concentrically withdrawn into the nozzle. After the jet emerges from the drop, the liquid is accelerated by tangential sweeping forces exerted by the gas stream flowing on its surface, which gradually decreases the jet cross-section. Stated differently the gas flow acts as a lens and focuses and stabilizes the microjet as it moves toward and into the exit orifice of the pressure chamber.

The forces exerted by the second fluid flow on the first fluid surface should be steady enough to prevent irregular surface oscillations. Therefore, any turbulence in the gas motion should be avoided; even if the gas velocity is high, the characteristic size of the orifice should ensure that the gas motion is laminar (similar to the boundary layers formed on the jet and on the inner surface of the nozzle or hole).

STABLE MICROJET

FIG. 4 illustrates the interaction of a liquid and a gas to form atomizate using the method of the invention. The feeding needle 60 has a circular exit opening 61 with an internal radius $R_O$ which feeds a liquid 62 out of the end, forming a drop with a radius in the range of $R_O$ to $R_O$ plus the thickness of the wall of the needle. The exiting liquid forms an infinite amount of liquid streamlines 63 that interact with the surrounding gas to form a stable cusp at the interface 64 of the two fluids. The surrounding gas also forms an infinite number of gas streamlines 65, which interact with the exiting liquid to create a virtual focusing funnel 66. The exiting liquid is focused by the focusing funnel 66 resulting in a stable microjet 67, which remains stable until it exits the opening 68 of the pressure chamber 69. After exiting the pressure chamber, the microjet begins to break-up, forming monodispersed particles 70.

The gas flow, which affects the liquid withdrawal and its subsequent acceleration after the jet is formed, should be very rapid but also uniform in order to avoid perturbing the fragile capillary interface (the surface of the drop that emerges from the jet).

Liquid flows out of the end of a capillary tube and forms a small liquid drop at the end. The tube has an internal radius $R_o$ . The drop has a radius in a range of from $R_O$ to $R_O$ plus the structural thickness of the tube as the drop exits the tube, and thereafter the drop narrows in circumference to a much smaller circumference as is shown in the expanded view of the tube (i.e. feeding needle) 5 as shown in FIGS. 1 and 4.

As illustrated in FIG. 4, the exit opening 61 of the capillary tube 60 is positioned close to an exit opening 68 in a planar surface of a pressure chamber 69. The exit opening 68 has a minimum diameter D and is in a planar member with a thickness L. The diameter D is referred to as a minimum diameter because the opening may have a conical configuration with the narrower end of the cone positioned closer to the source of liquid flow. Thus, the exit opening may be a funnel-shaped nozzle although other opening configurations are also possible, e.g. an hour glass configuration. Gas in the pressure chamber continuously flows out of the exit opening. The flow of the gas causes the liquid drop expelled from the tube to decrease in circumference as the liquid moves away from the end of the tube in a direction toward the exit opening of the pressure chamber.

In actual use, it can be understood that the opening shape which provokes maximum gas acceleration (and consequently the most stable cusp and microjet with a given set of parameters) is a conically shaped opening in the pressure chamber. The conical opening is positioned with its narrower end toward the source of liquid flow.

The distance between the end 61 of the tube 60 and the beginning of the exit opening 68 is H. At this point it is noted that $R_0$, D, H and L are all preferably on the order of hundreds of microns. For example, $R_o$=400 μm, D=150 μm, H=1 mm, L=300 μm. However, each could be 1/100 to 100×these sizes.

The end of the liquid stream develops a cusp-like shape at a critical distance from the exit opening 68 in the pressure chamber 69 when the applied pressure drop $\Delta P_g$ across the exit opening 68 overcomes the liquid-gas surface tension stresses $\gamma/R^*$ appearing at the point of maximum curvature—e.g. $1/R^*$ from the exit opening.

A steady state is then established if the liquid flow rate Q ejected from the drop cusp is steadily supplied from the capillary tube. This is the stable capillary cusp which is an essential characteristic of the invention needed to form the stable microjet. More particularly, a steady, thin liquid jet with a typical diameter $d_j$. is smoothly emitted from the stable cusp-like drop shape and this thin liquid jet extends over a distance in the range of microns to millimeters. The length of the stable microjet will vary from very short (e.g. 1 micron) to very long (e.g. 50 mm) with the length depending on the (1) flow-rate of the liquid and (2) the Reynolds number of the gas stream flowing out of the exit opening of the pressure chamber. The liquid jet is the stable capillary microjet obtained when supercritical flow is reached. This jet demonstrates a robust behavior provided that the pressure drop $\Delta P_g$ applied to the gas is sufficiently large compared to the maximum surface tension stress (on the order of $\gamma/d_j$) that act at the liquid-gas interface. The jet has a slightly parabolic axial velocity profile which is, in large part, responsible for the stability of the microjet. The stable microjet is formed without the need for other forces, i.e. without adding force such as electrical forces on a charged fluid. However, for some applications it is preferable to add charge to particles, e.g. to cause the particles to adhere to a given surface. The shaping of liquid exiting the capillary tube by the gas flow forming a focusing funnel creates a cusp-like meniscus resulting in the stable microjet. This is a fundamental characteristic of the invention.

Figure 4:
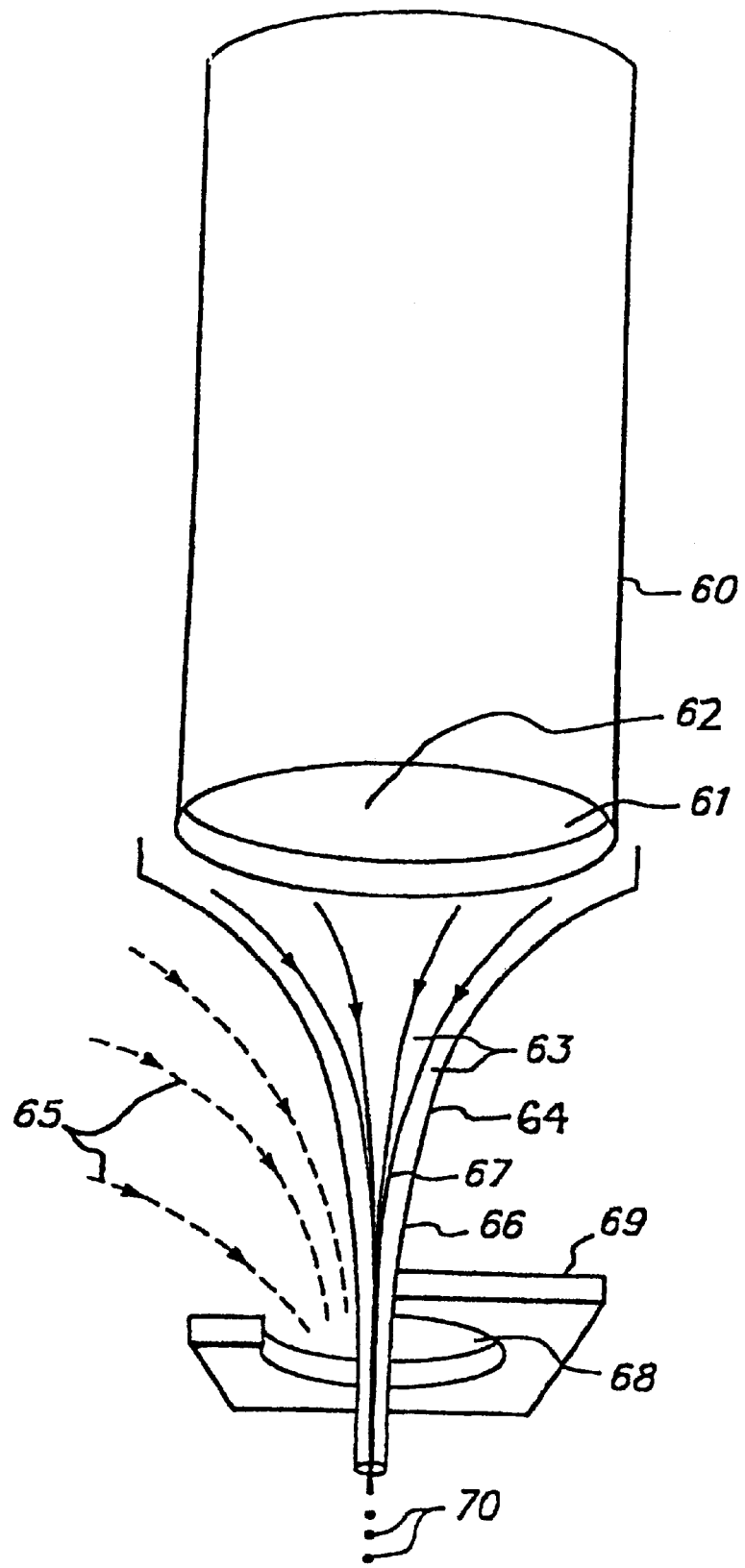
FIG. 4 is a schematic view of a stable capillary microjet being formed and flowing through an exit opening to thereafter form a monodisperse aerosol.
Figure 5:
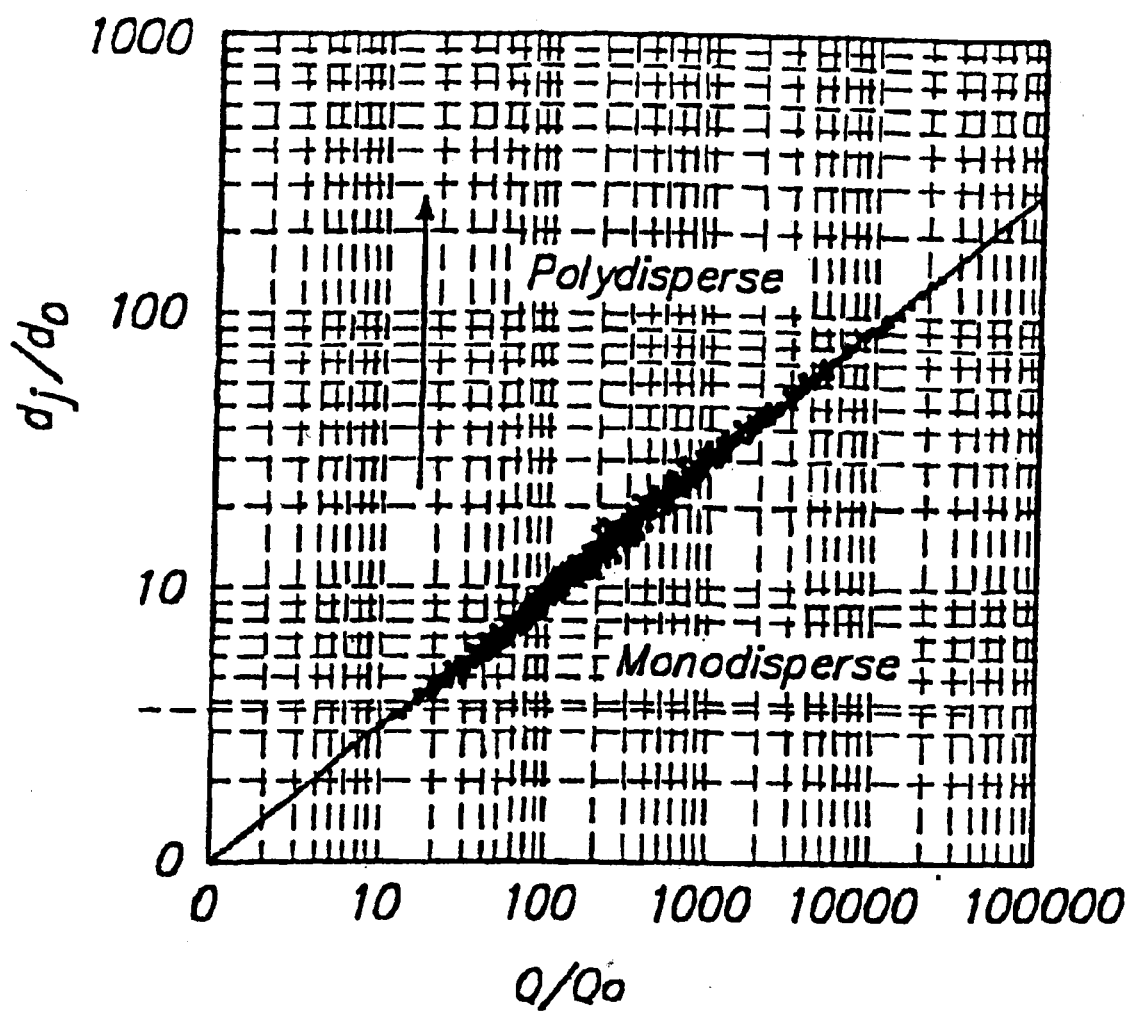
FIG. 5 is a graph of data where 350 measured values of $d_j/d_o$ versus $Q/Q_o$ are plotted.

The fluid stream flowing from the tube has substantially more density and develops substantially more inertia as compared to the gas, which has lower viscosity than the liquid. These characteristics contribute to the formation of the stable capillary jet. The stable capillary microjet is maintained stably for a significant distance in the direction of flow away from the exit from the tube. The liquid is, at this point, undergoing "supercritical flow." The microjet eventually destabilizes due to the effect of surface tension forces. Destabilization results from small natural perturbations moving downstream, with the fastest growing perturbations being those which govern the break up of the microjet, eventually creating a monodisperse (a uniform sized) aerosol 70 as shown in FIG. 4.

The microjet, even as it initially destabilizes, passes out of the exit orifice of the pressure chamber without touching the peripheral surface of the exit opening. This provides an important advantage of the invention which is that the exit opening 68 (which could be referred to as a nozzle) will not clog from residue and/or deposits of the liquid. Clogging is a major problem with very small nozzles and is generally dealt with by cleaning or replacing the nozzle. When fluid contacts the surfaces of a nozzle opening some fluid will remain in contact with the nozzle when the flow of fluid is shut off. The liquid remaining on the nozzle surface evaporates leaving a residue. After many uses over time the residue builds up and clogging takes place. The present invention substantially reduces or eliminates this clogging problem.

MATHEMATICS OF A STABLE MICROJET

Cylindrical coordinates (r,z) are chosen for making a mathematical analysis of a stable microjet, i.e. liquid undergoing "supercritical flow." The cusp-like meniscus formed by the liquid coming out of the tube is pulled toward the exit of the pressure chamber by a pressure gradient created by the flow of gas.

The cusp-like meniscus formed at the tube's mouth is pulled towards the hole by the pressure gradient created by the gas stream. From the cusp of this meniscus, a steady liquid thread with the shape of radius r=ξ is withdrawn through the hole by the action of both the suction effect due to $\Delta P_g$, and the tangential viscous stresses $\tau_5$ exerted by the gas on the jet's surface in the axial direction. The averaged momentum equation for this configuration may be written $$\frac{d}{d_z}\left[P_l + \frac{\rho_l Q^2}{2\Pi^2 \xi^4}\right] = \frac{2\tau_s}{\xi}, \quad (1)$$

where Q is the liquid flow rate upon exiting the feeding tube, $P_l$ is the liquid pressure, and $\rho_l$ is the liquid density, assuming that the viscous extensional term is negligible compared to the kinetic energy term, as will be subsequently justified. In addition, liquid evaporation effects are neglected. The liquid pressure $P_l$ is given by the capillary equation.

$$P_1 32\, P_g + \gamma/\xi. \quad (2)$$

where γ is the liquid-gas surface tension. As shown in the Examples, the pressure drop $\Delta P_g$ is sufficiently large as compared to the surface tension stress γ/ξ to justify neglecting the latter in the analysis. This scenario holds for the whole range of flow rates in which the microjet is absolutely stable. In fact, it will be shown that, for a given pressure drop $\Delta P_g$, the minimum liquid flow rate that can be sprayed in steady jet conditions is achieved when the surface tension stress γ/ξ is of the order of the kinetic energy of the liquid $\rho_l Q^2/(2\pi^2\xi^4)$, since the surface tension acts like a "resistance" to the motion (it appears as a negative term in the right-hand side term of Eq. (1)). Thus, $$Q_{\min} \sim \left(\frac{\gamma d_j^3}{\rho_l}\right)^{\frac{1}{2}} \quad (3)$$

For sufficiently large flow rates Q compared to $Q_{min}$, the simplified averaged momentum equation in the axial direction can be expressed as $$\frac{d}{d_z}\left(\frac{\rho_l Q^2}{2\Pi^2 \xi^4}\right) = \frac{dP_g}{d_z} + \frac{2\tau_s}{\xi}, \quad (4)$$

where one can identify the two driving forces for the liquid flow on the right-hand side. This equation can be integrated provided the following simplification is made: if one uses a thin plate with thickness L of the order or smaller than the hole's diameter D (which minimizes downstream perturbations in the gas flow), the pressure gradient up to the hole exit is on the average much larger than the viscous shear term $2\tau_5/\xi$ owning to the surface stress. On the other hand, the axial viscous term is of the order $O[\mu^2 Q/D^2 d_j^2]$, since the hole diameter D is actually the characteristic distance associated with the gas flow at the hole's entrance in both the radial and axial directions. This term is very small compared to the pressure gradient in real situations, provided that $\Delta P_g >> \mu^2/D^2\rho_1$ (which holds, e.g., for liquids with viscosities as large as 100 cpoises, using hole diameters and pressure drops as small as D~10 μm and "$P_g \geqq 100$ mbar). The neglect of all viscous terms in Eq. (4) is then justified. Notice that in this limit on the liquid flow is quasi-isentropic in the average (the liquid almost follows Bernoulli equation) as opposed to most micrometric extensional flows. Thus, integrating (4) from the stagnation regions of both fluids up to the exit, one obtains a simple and universal expression for the jet diameter at the hole exit:

$$d_j \simeq \left(\frac{8\rho_l}{\Pi^2 \Delta P_g}\right)^{\frac{1}{4}} Q^{\frac{1}{2}}, \quad (5)$$

which for a given pressure drop $\Delta P_g$ is independent of geometrical parameters (hole and tube diameters, tube-hole distance, etc.), liquid and gas viscosities, and liquid-gas surface tension. This diameter remains almost constant up to the breakup point since the gas pressure after the exit remains constant.

MONODISPERSE PARTICLES

Above the stable microjet undergoing "supercritical flow" is described and it can be seen how this aspect of the invention can be made use of in a variety of industrial applications—particularly where the flow of liquid through small holes creates a clogging problem. An equally important aspect of the invention is obtained after the microjet leaves the pressure chamber.

When the microjet exits the pressure chamber the liquid pressure $P_l$ becomes (like the gas pressure $P_g$) almost constant in the axial direction, and the jet diameter remains almost constant up to the point where it breaks up by capillary instability. Defining a Weber number We= $(\rho_g v_g^2 d_j)/\gamma \approx 2 \Delta P_g d_j/\gamma$ (where $v_g$ is the gas velocity measured at the orifice), below a certain experimental value $We_c \sim 40$ the breakup mode is axisymmetric and the resulting droplet stream is characterized by its monodispersity provided that the fluctuations of the gas flow do not contribute to droplet coalescence (these fluctuations occur when the gas stream reaches a fully developed turbulent profile around the liquid jet breakup region). Above this $We_c$ value, sinuous nonaxisymmetric disturbances, coupled to the axisymmetric ones, become apparent. For larger We numbers, the nonlinear growth rate of the sinuous disturbances seems to overcome that of the axisymmetric disturbances. The resulting spray shows significant polydispersity in this case. Thus, it can be seen that by controlling parameters to keep the resulting Weber number to 40 or less, allows the particles formed to be all substantially the same size. The size variation is about ±3% to ±30% and move preferably ±3% to ±10%. These particles can have a desired size e.g. 0.1 microns to 50 microns.

The shed vorticity influences the breakup of the jet and thus the formation of the particles. Upstream from the bole exit, in the accelerating region, the gas stream is laminar. Typical values of the Reynolds number range from 500 to 6000 if a velocity of the order of the speed of sound is taken as characteristic of the velocity of the gas. Downstream from the hole exit, the cylindrical mixing layer between the gas stream and the stagnant gas becomes unstable by the classical Kelvin-Helmholtz instability. The growth rate of the thickness of this layer depends on the Reynolds number of the flow and ring vortices are formed at a frequency of the order of $v_g/D$, where D is the hole diameter. Typical values of $v_g$ and D as those found in our experimental technique lead to frequencies or the order of MHZ which are comparable to the frequency of drop production (of order of $t_b^{-1}$).

Given the liquid flow rate and the hole diameter, a resonance frequency which depends on the gas velocity (or pressure difference driving the gas stream) can be adjusted (tuned) in such a way that vortices act as a forcing system to excite perturbations of a determined wavelength on the jet surface. Experimental results obtained clearly illustrates the different degree of coupling between the two gas-liquid coaxial jets. In one set of experimental results the particle sizes are shown to have a particle size of about 5.7 microns with a standard deviation of 12%. This results when the velocity of the gas has been properly tuned to minimize the dispersion in the size of droplets resulting from the jet breakup. In this case, the flow rate of the liquid jet and its diameter are 0.08 $\mu l\ s^{-1}$ and 3 $\mu$m, respectively. Data have been collected using a MASTERSIZER from MALVERN Instruments. As the degree of coupling decreases, perturbations at the jet surface of different wavelengths become excited and, as it can be observed from the size distributions, the dispersion of the spray increases.

It is highly desirable in a number of different industrial applications to have particles which are uniform in size or to create aerosols of liquid particles which are uniform in size. For example, particles of a liquid formation containing a pharmaceutically active drug could be created and designed to have a diameter of about 2 microns ±3%. These particles could be inhaled into the lungs of a patient for intrapulmonary drug delivery. Moreover, particle size can be adjusted to target a particular area of the respiratory tract.

The gas flow should be laminar in order to avoid a turbulent regime-turbulent fluctuations in the gas flow which have a high frequency and would perturb the liquid-gas interface. The Reynolds numbers reached at the orifice are $$Re = \frac{V_g d_0}{v_g} \sim 4000$$

where $V_g$ is the velocity of the gas and where $v_g$ is the kinematic viscosity of the gas. Even though this number is quite high, there are large pressure gradients downstream (a highly convergent geometry), so that a turbulent regime is very unlikely to develop.

The essential difference from existing pneumatic atomizers (which possess large Weber numbers) and the present invention is that the aim of the present invention is not to rupture the liquid-gas interface but the opposite, i.e. to increase the stability of the interface until a capillary jet is obtained. The jet, which will be very thin provided the pressure drop resulting from withdrawal is high enough, splits into drops the sizes of which are much more uniform than those resulting from disorderly breakage of the liquid-gas interface in existing pneumatic atomizers.

The proposed atomization system obviously requires delivery of the liquid to be atomized and the gas to be used in the resulting spray. Both should be fed at a rate ensuring that the system lies within the stable parameter window. Multiplexing is effective when the flow-rates needed exceed those on an individual cell. More specifically, a plurality of feeding sources or feeding needles may be used to increase the rate at which aerosols are created. The flow-rates used should also ensure the mass ratio between the flows is compatible with the specifications of each application.

The gas and liquid can be dispensed by any type of continuous delivery system (e.g. a compressor or a pressurized tank the former and a volumetric pump or a pressurized bottle the latter). If multiplexing is needed, the liquid flow-rate should be as uniform as possible among cells; this may entail propulsion through several capillary needles, porous media or any other medium capable of distributing a uniform flow among different feeding points.

Each individual atomization device should consist of a feeding point (a capillary needle, a point with an open microchannel, a microprotuberance on a continuous edge, etc.) 0.002–2 mm (but, preferentially 0.01–0.4 mm) in diameter, where the drop emerging from the microjet can be anchored, and a small orifice 0.002–2 mm (preferentially 0.01–0.25 mm) in diameter facing the drop and separated 0.01–2 mm (preferentially 0.2–0.5 mm) from the feeding point. The orifice communicates the withdrawal gas around the drop, at an increased pressure, with the zone where the atomizate is produced, at a decreased pressure. The atomizer can be made from a variety of materials (metal, polymers, ceramics, glass).

FIG. 1 depicts a tested prototype where the liquid to be atomized is inserted through one end of the system 2 and the propelling gas in introduced via the special inlet 4 in the pressure chamber 3. The prototype was tested at gas feeding rates from 100 to 2000 mBar above the atmospheric pressure $P_a$ at which the atomized liquid was discharged. The whole enclosure around the feeding needle 1 was at a pressure $P_O > P_a$. The liquid feeding pressure, $P_l$, should always be slightly higher than the gas propelling pressure, $P_O$. Depending on the pressure drop in the needle and the liquid feeding system, the pressure difference ($P_l - P_O > 0$) and the flow-rate of the liquid to be atomized, Q, are linearly related provided the flow is laminar—which is indeed the case with this prototype. The critical dimensions are the distance from the needle to the plate (H), the needle diameter ($D_O$), the diameter of the orifice through which the microjet 6 is discharged ($d_O$) and the axial length, e, of the orifice (i.e. the thickness of the plate where the orifice is made). In this prototype, H was varied from 0.3 to 0.7 mm on constancy of the distances ($D_O$=0.45 mm, $d_O$–0.2 mm) and e–0.5 mm. The quality of the resulting spray 7 did not vary appreciably with changes in H provided the operating regime (i.e. stationary drop and microjet) was maintained. However, the system stability suffered at the longer H distances (about 0.7 mm). The other atomizer dimensions had no effect on the spray or the prototype functioning provided the zone around the needle (its diameter) was large enough relative to the feeding needle. As explained further below it is possible to obtain a stable capillary microjet which does not disassociate into a monodisperse aerosol. However, by adjusting parameters which relate to the Weber number a stable microjet is formed which disassociates to monodisperse aerosol.

WEBER NUMBER

Adjusting parameters to obtain a stable capillary microjet and control its breakup into monodisperse particle is governed by the Weber number and the liquid-to-gas velocity ratio or α which equal $V_l/V_g$. The Weber number or "We" is defined by the following equation:

$$We = \frac{\rho_g V_g^2 d}{\gamma}$$

wherein $\rho_g$ is the density of the gas, d is the diameter of the stable microjet, γ is the liquid-gas surface tension, and $V_g^2$ is the velocity of the gas squared.

When carrying out the invention the parameters should be adjusted so that the Weber number is greater than 1 in order to produce a stable capillary microjet. However, to obtain a particle dispersion which is monodisperse (i.e. each particle has the same size ±3 to ±30%) the parameters should be adjusted so that the Weber number is less than 40. The monodisperse aerosol is obtained with a Weber number in a range of about 1 to about 40 when the breaking time is sufficiently small to avoid non-symmetric perturbations. (1≦We≦40)

OHNESORGE NUMBER

A measure of the relative importance of viscosity on the jet breakup can be estimated from the Ohnesorge number defined as the ratio between two characteristic times: the viscous time $t_v$ and the breaking time $t_b$. The breaking time $t_b$ is given by [see Rayleigh (1878)]

$$t_b \sim \left(\frac{\rho_l d^2}{\gamma}\right)^{\frac{1}{2}}. \tag{2}$$

Perturbations on the jet surface are propagated inside by viscous diffusion in times $t_v$ of the order of $$t_v \sim \rho_1 d^2/\mu_1 \tag{3}$$

where $\mu_l$ is the viscosity of the liquid. Then, the Ohnesorge number, Oh, results $$Oh = \frac{\mu_l}{(\rho_l \gamma d)^{\frac{1}{2}}}. \tag{4}$$

If this ratio is much smaller than unity viscosity plays no essential role in the phenomenon under consideration. Since the maximum value of the Ohnesorge number in actual experiments conducted is as low as $3.7 \times 10^{-2}$, viscosity plays no essential role during the process of jet breakup.

EMBODIMENT OF FIG. 2

A variety of configurations of components and types of fluids will become apparent to those skilled in the art upon reading this disclosure. These configurations and fluids are encompassed by the present invention provided they can produce a stable capillary microjet of a first fluid from a source to an exit port of a pressure chamber containing a second fluid. The stable microjet is formed by the first fluid flowing from the feeding source to the exit port of the pressure chamber being accelerated and stabilized by tangential viscous stress exerted by the second fluid in the pressure chamber on the surface of the first fluid forming the microjet. The second fluid forms a focusing funnel when a variety of parameters are correctly tuned or adjusted. For example, the speed, pressure, viscosity and miscibility of the first and second fluids are chosen to obtain the desired results of a stable microjet of the first fluid focused into the center of a funnel formed with the second fluid. These results are also obtained by adjusting or tuning physical parameters of the device, including the size of the opening from which the first fluid flows, the size of the opening from which both fluids exit, and the distance between these two openings.

Figure 2:
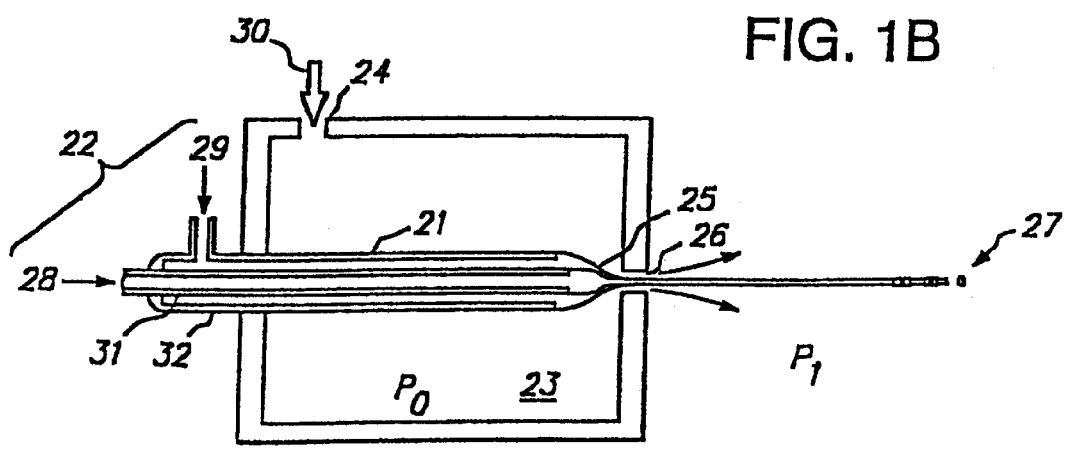
FIG. 2 is a schematic view of another embodiment of the invention with two concentric tubes as a source of formulation.

The embodiment of FIG. 1 can, itself, be arranged in a variety of configurations. Further, as indicated above, the embodiment may include a plurality of feeding needles. A plurality of feeding needles may be configured concentrically in a single construct, as shown in FIG. 2.

The concentrically positioned feeding needle preferable extrude liquids which are not misable in each other, e.g. oil and water. The feeding needles can be designed and have fluid flowing through them so as to result in the creation of a plurality of concentrical spheres, i.e. a sphere inside a sphere inside another sphere etc. The stability of the concentrical spheres can be maintained by a number of procedures. For example, the concentrical spheres are blown into a curing tube. The spheres move through the tube and are irradiated by energy which cures, hardens or polymerizes sphere coating which then prevent the liquids held in the different coating spheres from intermixing.

An internal solid sphere of lactose could be coated with a polymer coating which would not dissolve in a dairy product (e.g. milk or ice cream) but would dissolve in the G.I. tract. Thus, the lactose of the dairy product would combine with the lactase enzyme after being consumed. This would make it possible for lactose intolerant individuals to eat dairy products.

The internal sphere could be gas (e.g. air or nitrogen) held by a polymer coating shell. The shell could have a coating which is high in fat, flavor, sweet taste etc. thereon. By spreading the coating over a large area, the effect of it is amplified when the particles are dispersed uniformly in a food product.

The components of the embodiment of FIG. 2 are as follows:

21. Feeding needle-tube or source of fluid.
22. End of the feeding needle used to insert the liquids to be atomized.
23. Pressure chamber.
24. Orifice used as gas inlet.
25. End of the feeding needle used to evacuate the liquid to be atomized.
26. Orifice through which withdrawal takes place.
27. Atomizate (spray) or aerosol.
28. First liquid to be atomized (inner core of particle).
29. Second liquid to be atomized (outer coating of particle).
30. Gas for creation of microjet.
31. Internal tube of feeding needle.
32. External tube of feeding needle.

D=diameter of the feeding needle; d=diameter of the orifice through which the microjet is passed; e=axial length of the orifice through which withdrawal takes place; H=distance from the feeding needle to the microjet outlet; γ=surface tension; $P_O$=pressure inside the chamber; $P_a$=atmospheric pressure.

The embodiment of FIG. 2 is preferably used when attempting to form a spherical particle of one substance coated by another substance, e.g. a sweet tasting substance surrounding a bitter tasting substance. The device of FIG. 2 is comprised of the same basic component as per the device of FIG. 1 and further includes a second feeding source 32 which is positioned concentrically around the first cylindrical feeding source 31. The second feeding source may be surrounded by one or more additional feeding sources with each concentrically positioned around the preceding source. The outer coating may be used for a variety of purposes, including: coating particles to prevent small particles from sticking together; to obtain a sustained release effect of the active compound (e.g. a pharmaceutically active drug) inside, and/or to mask flavors; and to protect the stability of another compound (e.g. a pharmaceutically active drug) contained therein.

The process is based on the microsuction which the liquid-gas or liquid-liquid interphase undergoes (if both are immiscible), when said interphase approaches a point beginning from which one of the fluids is suctioned off while the combined suction of the two fluids is produced. The interaction causes the fluid physically surrounded by the other to form a capillary microjet which finally breaks into spherical drops. If instead of two fluids (gas-liquid), three or more are used that flow in a concentric manner by injection using concentric tubes, a capillary jet composed of two or more layers of different fluids is formed which, when it breaks, gives rise to the formation of spheres composed of several approximately concentric spherical layers of different fluids. The size of the outer sphere (its thickness) and the size of the inner sphere (its volume) can be precisely adjusted. This can allow the manufacture of coated particles for a variety of end uses. For example the thickness of the coating can be varied in different manufacturing events to obtain coated particles which have gradually decreasing thicknesses to obtain a controlled release effect of the contents, e.g. a nutritional food or a pharmaceutically active drug. The coating could merely prevent the particles from degrading, reacting, or sticking together.

The method is based on the breaking of a capillary microjet composed of a nucleus of one liquid or gas and surrounded by another or other liquids and gases which are in a concentric manner injected by a special injection head, in such a way that they form a stable capillary microjet and that they do not mix by diffusion during the time between when the microjet is formed and when it is broken. When the capillary microjet is broken into spherical drops under the proper operating conditions, which will be described in detail below, these drops exhibit a spherical nucleus, the size and eccentricity of which can be controlled.

In the case of spheres containing two materials, the injection head 25 consists of two concentric tubes with an external diameter on the order of one millimeter. Through the internal tube 31 is injected the material that will constitute the nucleus of the microsphere, while between the internal tube 31 and the external tube 32 the coating is injected. The fluid of the external tube 32 joins with the fluid of tube 31 as the fluids exit the feeding needle, and the fluids (normally liquids) thus injected are accelerated by a stream of gas that passes through a small orifice 24 facing the end of the injection tubes. When the drop in pressure across the orifice 24 is sufficient, the liquids form a completely stationary capillary microjet, if the quantities of liquids that are injected are stationary. This microjet does not touch the walls of the orifice, but passes through it wrapped in the stream of gas or funnel formed by gas from the tube 32. Because the funnel of gas focuses the liquid, the size of the exit orifice 26 does not dictate the size of the particles formed.

When the parameters are correctly adjusted, the movement of the liquid is uniform at the exit of the orifice 26 and the viscosity forces are sufficiently small so as not to alter either the flow or the properties of the liquids; for example, if there are biochemical molecular specimens having a certain complexity and fragility, the viscous forces that would appear in association with the flow through a micro-orifice might degrade these substances.

FIG. 2 shows a simplified diagram of the feeding needle 21, which is comprised of the concentric tubes 30, 31 through the internal and external flows of the fluids 28, 29 that are going to compose the microspheres comprised of two immiscible fluids. The difference in pressures $P_0-P_a$ ($P_O>P_a$) through the orifice 26 establishes a flow of gas present in the chamber 23 and which is going to surround the microjet at its exit. The same pressure gradient that moves the gas is the one that moves the microjet in an axial direction through the hole 26, provided that the difference in pressures $P_O-P_a$ is sufficiently great in comparison with the forces of surface tension, which create an adverse gradient in the direction of the movement.

In any operation of the device, the exit hole may be supplemented with (1) a temperature control means (e.g. a heater) and/or (2) a vibrational energy generating means. The heater could, for example, prevent the formulation of unwanted condensation on the opening hole 26. The vibrational energy generating means could serve to break up the stable microjet into smaller and more uniform particles than would form without the vibrational energy. The frequency of the vibration can be set to obtain a desired particle size and the heater temperature can be adjusted.

There are two limitations for the minimum sizes of the inside and outside jets that are dependent (a) on the surface tensions γ1 of the outside liquid 29 with the gas 30 and γ2 of the outside liquid 29 with the inside liquid 28, and (b) on the difference in pressures $\Delta P=P_O-P_a$ through the orifice 26. In the first place, the jump in pressures AP must be sufficiently great so that the adverse effects of the surface tension are minimized. This, however, is attained for very modest pressure increases: for example, for a 10 micron jet of a liquid having a surface tension of 0.05 N/m (tap water), the necessary minimum jump in pressure is in the order of 0.05 (N/m)/ 0.00001 m=ΔP=50 mBar. But, in addition, the breakage of the microjet must be regular and axilsymmetric, so that the drops will have a uniform size, while the extra pressure ΔP cannot be greater than a certain value that is dependent on the surface tension of the outside liquid with the gas γ1 and on the outside diameter of the microjet. It has been experimentally shown that this difference in pressures cannot be greater than 20 times the surface tension γ1 divided by the outside radius of the microjet.

Therefore, given some inside and outside diameters of the microjet, there is a range of operating pressures between a minimum and a maximum; nonetheless, experimentally the best results are obtained for pressures in the order of two to three times the minimum.

The viscosity values of the liquids must be such that the liquid with the greater viscosity $\mu_{max}$ verifies, for a diameter d of the jet predicted for this liquid and a difference through the orifice ΔP, the inequality:

$$\mu_{\max} \leq \frac{\Delta P d^2 D}{Q}$$

With this, the pressure gradients can overcome the extensional forces of viscous resistance exerted by the liquid when it is suctioned toward the orifice.

Moreover, the liquids must have very similar densities in order to achieve the concentricity of the nucleus of the microsphere, since the relation of velocities between the liquids moves according to the square root of the densities $v1/v2=(\rho 2/\rho 1)^{1/2}$ and both jets, the inside jet and the outside jet, must assume the most symmetrical configuration possible, which does not occur if the liquids have different velocities (FIG. 2). Nonetheless, it has been experimentally demonstrated that, on account of the surface tension γ2 between the two liquids, the nucleus tends to migrate toward the center of the microsphere, within prescribed parameters.

When two liquids and gas are used on the outside, the distance between the planes of the mouths of the concentric tubes can vary, without the characteristics of the jet being substantially altered, provided that the internal tube 31 is not introduced into the external one 32 more than one diameter of the external tube 32 and provided that the internal tube 31 does not project more than two diameters from the external tube 32. The best results are obtained when the internal tube 31 projects from the external one 32 a distance substantially the same as the diameter of the internal tube 31. This same criterion is valid if more than two tubes are used, with the tube that is surrounded (inner tube) projecting beyond the tube that surrounds (outer tube) by a distance substantially the same as the diameter of the first tube.

The distance between the plane of the internal tube 31 (the one that will normally project more) and the plane of the orifice may vary between zero and three outside diameters of the external tube 32, depending on the surface tensions between the liquids and with the gas, and on their viscosity values. Typically, the optimal distance is found experimentally for each particular configuration and each set of liquids used.

The proposed atomizing system obviously requires fluids that are going to be used in the resulting spray to have certain flow parameters. Accordingly, flows for this use must be:

Flows that are suitable so that the system falls within the parametric window of stability. Multiplexing (i.e. several sets of concentric tubes) may be used, if the flows required are greater than those of an individual cell.

Flows that are suitable so that the mass relation of the fluids falls within the specifications of each application. Of course, a greater flow of gas may be supplied externally by any means in specific applications, since this does not interfere with the functioning of the atomizer.

If the flows are varied, the characteristic time of this variation must be less than the hydrodynamic residence times of liquid and gas in the microjet, and less than the inverse of the first natural oscillation frequency of the drop formed at the end of the injection needle.

Therefore, any means for continuous supply of gas (compressors, pressure deposits, etc.) and of liquid (volumetric pumps, pressure bottles) may be used. If multiplexing is desired, the flow of liquid must be as homogeneous as possible between the various cells, which may require impulse through multiple capillary needles, porous media, or any other medium capable of distributing a homogeneous flow among different feeding points.

Each atomizing device will consist of concentric tubes 31, 32 with a diameter ranging between 0.05 and 2 mm, preferably between 0.1 and 0.4 mm, on which the drop from which the microjet emanates can be anchored, and a small orifice (between 0.001 and 2 mm in diameter, preferably between 0.1 and 0.25 mm), facing the drop and separated from the point of feeding by a distance between 0.001 and 2 mm, preferably between 0.2 and 0.5 mm. The orifice puts the suction gas that surrounds the drop, at higher pressure, in touch with the area in which the atomizing is to be attained, at lower pressure.

EMBODIMENT OF FIG. 3

The embodiments of FIGS. 1 and 2 are similar in a number of ways. Both have a feeding piece which is preferably in the form of a feeding needle with a circular exit opening. Further, both have an exit port in the pressure chamber which is positioned directly in front of the flow path of fluid out of the feeding source. Precisely maintaining the alignment of the flow path of the feeding source with the exit port of the pressure chamber can present an engineering challenge particularly when the device includes a number of feeding needles. The embodiment of FIG. 3 is designed to simplify the manner in which components are aligned. The embodiment of FIG. 3 uses a planar feeding piece (which by virtue of the withdrawal effect produced by the pressure difference across a small opening through which fluid is passed) to obtain multiple microjets which are expelled through multiple exit ports of a pressure chamber thereby obtaining multiple aerosol streams. Although a single planar feeding member as shown in FIG. 3 it, of course, is possible to produce a device with a plurality of planar feeding members where each planar feeding member feeds fluid to a linear array of outlet orifices in the surrounding pressure chamber. In addition, the feeding member need not be strictly planar, and may be a curved feeding device comprised of two surfaces that maintain approximately the same spatial distance between the two pieces of the feeding source. Such curved devices may have any level of curvature, e.g. circular, semicircular, elliptical, hemi-elliptical, etc.

The components of the embodiment of FIG. 3 are as follows:

41. Feeding piece.

42. End of the feeding piece used to insert the fluid to be atomized.

43. Pressure chamber.

44. Orifice used as gas inlet.
45. End of the feeding needle used to evacuate the liquid to be atomized.
46. Orifices through which withdrawal takes place.
47. Atomizate (spray) or aerosol.
48. first fluid containing material to be atomized.
49. second fluid for creation of microjet.
50. wall of the propulsion chamber facing the edge of the feeding piece.
51. channels for guidance of fluid through feeding piece.

$d_j$=diameter of the microjet formed; $\rho_A$=liquid density of first fluid (48); $\rho_B$=liquid density of second fluid (49); $v_A$=velocity of the first liquid (48); $v_B$=velocity of the second liquid (49); e=axial length of the orifice through which withdrawal takes place; H=distance from the feeding needle to the microjet outlet; $P_O$=pressure inside the chamber;

$\Delta P_g$=change in pressure of the gas; $P_a$=atmospheric pressure; Q=volumetric flow rate The proposed dispersing device consists of a feeding piece 41 which creates a planar feeding channel through which a where a first fluid 48 flows. The flow is preferably directed through one or more channels of uniform bores that are constructed on the planar surface of the feeding piece 41. A pressure chamber 43 that holds the propelling flow of a second liquid 49, houses the feeding piece 41 and is under a pressure above maintained outside the chamber wall 50. One or more orifices, openings or slots (outlets) 46 made in the wall 52 of the propulsion chamber face the edge of the feeding piece. Preferably, each bore or channel of the feeding piece 41 has its flow path substantially aligned with an outlet 46.

Formation of the microjet and its acceleration are based on the abrupt pressure drop resulting from the steep acceleration undergone by the second fluid 49 on passing through the orifice 46, similarly to the procedure described above for embodiments of FIGS. 1 and 2 when the second fluid 49 is a gas.

When the second fluid 49 is a gas and the first fluid 48 is a liquid, the microthread formed is quite long and the liquid velocity is much smaller than the gas velocity. In fact, the low viscosity of the gas allows the liquid to flow at a much lower velocity; as a result, the microjet is actually produced and accelerated by stress forces normal to the liquid surface, i.e. pressure forces. Hence, one effective approximation to the phenomenon is to assume that the pressure difference established will result in the same kinetic energy per unit volume for both fluids (liquid and gas), provided gas compressibility effects are neglected. The diameter $d_j$ of the microjet formed from a liquid density $\rho_l$ that passes at a volumetric flow-rate Q through an orifice across which a pressure difference $\Delta P_g$ exists will be given by $$d_j \cong \left(\frac{8\rho_l}{\pi^2 \Delta P_g}\right)^{\frac{1}{4}} Q^{\frac{1}{2}}$$

See Gañàn-Calvo, *Physical Review Letters*, 80:285–288 (1998).

The relation between the diameter of the microjet, $d_j$, and that of the resulting drops, $\bar{d}$, depends on the ratio between viscous forces and surface tension forces on the liquid on the one hand, and between dynamic forces and surface tension forces on the gas on the other (i.e. on the Ohnesorge and Weber numbers, respectively) (Hinds (*Aerosol Technology*, John & Sons, 1982), Lefevre (*Atomization and Sprays*, Hemisphere Pub. Corp., 1989) and Bayvel & Orzechowski (*Liquid Atomization*, Taylor & Francis, 1993)). At moderate to low gas velocities and low viscosities the relation is roughly identical with that for capillarity instability developed by Rayleigh:

$$\bar{d} = 1.89 d_j$$

Because the liquid microjet is very long, at high liquid flow-rates the theoretical rupture point lies in the turbulent zone created by the gas jet, so turbulent fluctuations in the gas destabilize or rupture the liquid microjet in a more or less uneven manner. As a result, the benefits of drop size uniformity are lost.

On the other hand, when the second fluid 49 is a liquid and the first fluid 48 is a gas, the facts that the liquid is much more viscous and that the gas is much less dense virtually equalize the fluid and gas velocities. The gas microthread formed is much shorter; however, because its rupture zone is almost invariably located in a laminar flowing stream, dispersion in the size of the microbubbles formed is almost always small. At a volumetric gas flow-rate $Q_g$ and a liquid overpressure $\Delta P_l$, the diameter of the gas microjet is given by $$d_j \cong \left(\frac{8\rho_l}{\pi^2 \Delta P_l}\right)^{\frac{1}{4}} Q_g^{\frac{1}{2}}$$

The low liquid velocity and the absence of relative velocities between the liquid and gas lead to the Rayleigh relation between the diameters of the microthread and those of the bubbles (i.e. $d=1.89 d_j$). The above equation applies accurately when the inner fluid is liquid and the outer fluid is gas. However, when the inner fluid is gas and the outer fluid is a liquid, the above equation may not apply for a number a reasons. For example, the liquid does not move faster than the gas being focused to a microjet. However, the invention does make it possible to narrowly focus a stream of gas using a surrounding pressurized liquid. Further, the focused stream of gas does break up to form small bubbles which are substantially uniform in size. The bubbles are smaller and more uniform than if the outer liquid were not present.

If both fluids 48, 49 are liquid and scarcely viscous, then their relative velocities will be given by $$\frac{v_A}{v_B} = \left(\frac{\rho_B}{\rho_A}\right)^{\frac{1}{2}}$$

The diameter of a microjet of the first liquid at a volumetric flow-rate of A $Q_A$ and an overpressure of $\Delta P_B$ will be given by $$d_j \cong \left(\frac{8\rho_A}{\pi^2 \Delta P_B}\right)^{\frac{1}{4}} Q_A^{\frac{1}{2}}$$

At viscosities such that the velocities of both fluids 48, 49 will rapidly equilibrate in the microjet, the diameter of the microjet of the first liquid will be given by $$d_j \cong \left(\frac{8\rho_B}{\pi^2 \Delta P_B}\right)^{\frac{1}{4}} Q_A^{\frac{1}{2}}$$

The proposed atomization system obviously requires delivery of the fluids 48, 49 to be used in the dispersion process at appropriate flow-rates. Thus:

(1) Both flow-rates should be adjusted for the system so that they lie within the stable parameter window.

(2) The mass ratio between the flows should be compatible with the specifications of each application. Obviously, the gas flow-rate can be increased by using an external means in special applications (e.g. burning, drug inhalation) since this need not interfere with the atomizer operation.

(3) If the flow-rates are altered, the characteristic time for the variation should be shorter than the hydrodynamic residence times for the liquid and gas in the microjet, and smaller than the reciprocal of the first natural oscillation frequency of the drop formed at the end of the feeding piece.

(4) Therefore, the gas and liquid can be dispensed by any type of continuous delivery system (e.g. a compressor or a pressurized tank the former and a volumetric pump or a pressurized bottle the latter).

(5) The atomizer can be made from a variety of materials (metal, polymers, ceramics, glass).

FORMULATION COMPOSITION OF PARTICLES OF THE INVENTION

A number of different components can be added to foods using the technology of the present invention. The following are exemplary components that may be added to the formulations of the particles to be added to foods. The functional components may be used alone or in combination in the particles, which can be designed and sized for increased bioavailablity of the particles. In addition, functional components may be found in the center of a coated particle, as a layer in a multi-layered particle, or as the coating of a particle or hollow sphere.

Formulation components may also be inert materials that serve to coat a functional particle, provide controlled release of the functional components of a particle, or provide a filler as a template to be coated with a composition containing a functional particle.

The described components are not intended to be all-inclusive, and it is well within the skill of one in the art to identify other components that may be used in the invention upon reading the present specification.

Herbal Extracts

The passage of the Dietary Supplement Health and Education Act of 1994 (DSHEA) has stimulated the inclusion of a variety of herbs and botanicals into numerous functional food products, including beverages, chewing gums and sports bars. Herbal extracts and/or the functional components of such may be added to foods using the device of the invention. This includes herbal extracts purported to stimulate mental acuity, such as ginkgo biloba, those that provide energy, such as ginseng and guarana, those that build lean muscle mass, such as chromium picolinate and creatine, those that promote weight loss, such as caffeine, ephedrine and Ma Huang, and those that stimulate the immune system, such as echinacea. Additional extracts include, but are not limited to: bilberry extract, pine bark extract, garlic extract, green tea extract, turmeric, yeast extract, algae extract, royal jelly extract, tea extract; caffeine, kola nut extract, zinc, grape seed extract, flavonoids, yohimbe, milk thistle extract, bee pollen, etc.

Functional Components

Scientists have recently turned their attention to the health benefits of non-nutritive food components, such as those in plant foods, as non-nutritive dietary components for use in disease prevention. Although much of the research focus on these phytochemicals has been directed at their cancer chemoprevention properties, biologically-active plant components may be important in reducing risk for other chronic diseases, including osteoporosis and heart disease. Phytochemicals and/or other functional components that provide beneficial physiological results can be incorporated into functional food to bring these benefits to consumers.

In one example, sitostanol ester added to yellow fats has been shown to reduce cholesterol. *New Englan J Med* 1995. Other bioactive ingredients such as omega-3-fatty acids, and bifidogenic dietary fibers (e.g. Raftiline) may be used in yellow fats to lower cholesterol and/or fight cardiovascular disease.

In yet another example, functional components may ease the symptoms of menopause, such as night sweats and hot flashes. The addition of 'phytoestrogens' to food helps to reduce hot flashes and night sweats in women. These functional components can be added to foods to help ease these symptoms in women suffering from such discomfort.

Additional exemplary functional components can be found in Table 1, and include: carotenoids, collagen hydrolysate, dietary fiber, fatty acids, flavonoids, glucosinolates, indoles, isothiocyanates, phenols, plant sterols, prebiotics/probiotics, saponins, soy proteins, sulfides, thiols, tannins, etc.

Pharmaceutical Additives

Excipient Material

Formulations of the invention may comprise different amounts and ratios of food components and excipient material. Numerous different excipients can be used. Upon reading the disclosure those skilled in the art will come to understand the general concepts of the invention and will recognize that other excipients, amounts, ratios and combinations might be used to obtain the results first shown here.

A typical formulation of the invention will contain about 50% to 100% by weight of food component and a particularly preferred formulation will comprise 80 % by weight of the food component. Assuming a formulation with 80% by weight of food component with the remaining 20% being excipient material there are a number of possible components which could be used to make up that 20%.

Those skilled in the art and reading this disclosure will recognize that there are endless possibilities in terms of formulations. Even if the formulations are limited to the relatively few compounds shown above the formulation could be changed in limitless ways by adjusting the ratios of the components to each other.

Controlled Release Formulations

One necessary characteristic of a controlled release formulation is that it does not release all of the active ingredient at one time but rather releases the active ingredient gradually over time. This is particularly important when (1) the component has a relatively short half life and (2) a desired level of the component in blood serum must be maintained over a long period to obtain the desired effect. If all of the component is released at once it will all enter the circulatory system at once and be metabolized in the liver thereby causing the serum level to drop below the desired level.

Controlled release within the scope of this invention can be taken to mean any one of a number of extended release dosage forms. The following terms may be considered to be substantially equivalent to controlled release, for the purposes of the present invention: continuous release, controlled release, delayed release, depot, gradual release, long-term release, programmed release, prolonged release, proportionate release, protracted release, repository, retard, slow release, spaced release, sustained release, time coat, timed release, delayed action, extended action, layered-time action, long acting, prolonged action, repeated action, slowing acting, sustained action, sustained-action medications, and extended release.

Further discussions of these terms may be found in Lesczek Krowczynski, *Extended-Release Dosage Forms,* 1987 (CRC Press, Inc.).

The various controlled release technologies cover a very broad spectrum of drug dosage forms. Controlled release technologies include, but are not limited to physical systems and chemical systems.

Physical systems include, but are not limited to, reservoir systems with rate-controlling membranes, such as microencapsulation, macroencapsulation, and membrane systems; reservoir systems without rate-controlling membranes, such as hollow fibers, ultra microporous cellulose triacetate, and porous polymeric substrates and foams; monolithic systems, including those systems physically dissolved in non-porous, polymeric, or elastomeric matrices (e.g., nonerodible, erodible, environmental agent ingression, and degradable), and materials physically dispersed in non-porous, polymeric, or elastomeric matrices (e.g., nonerodible, erodible, environmental agent ingression, and degradable); laminated structures, including reservoir layers chemically similar or dissimilar to outer control layers; and other physical methods, such as osmotic pumps, or adsorption onto ion-exchange resins and such system may be ingestable, implantable implants, transdermal devices, etc.

Chemical systems include, but are not limited to, chemical erosion of polymer matrices (e.g., heterogeneous, or homogeneous erosion), or biological erosion of a polymer matrix (e.g., heterogeneous, or homogeneous). Additional discussion of categories of systems for controlled release may be found in Agis F. Kydonieus, *Controlled Release Technologies: Methods, Theory and Applications,* 1980 (CRC Press, Inc.).

Controlled release drug delivery systems may also be categorized under their basic technology areas, including, but not limited to, rate-preprogrammed drug delivery systems, activation-modulated drug delivery systems, feedback-regulated drug delivery systems, and site-targeting drug delivery systems.

In rate-preprogrammed drug delivery systems, release of drug molecules from the delivery systems "preprogrammed" at specific rate profiles. This may be accomplished by system design, which controls the molecular diffusion of drug molecules in and/or across the barrier medium within or surrounding the delivery system. Fick's laws of diffusion are often followed.

In activation-modulated drug delivery systems, release of drug molecules from the delivery systems is activated by some physical, chemical or biochemical processes and/or facilitated by the energy supplied externally. The rate of drug release is then controlled by regulating the process applied, or energy input.

In feedback-regulated drug delivery systems, release of drug molecules from the delivery systems may be activated by a triggering event, such as a biochemical substance, in the body. The rate of drug release is then controlled by the concentration of triggering agent detected by a sensor in the feedback regulated mechanism.

In a site-targeting controlled-release drug delivery system, the drug delivery system targets the active molecule to a specific site or target tissue or cell. This may be accomplished, for example, by a conjugate including a site specific targeting moiety that leads the drug delivery system to the vicinity of a target tissue (or cell), a solubilizer that enables the drug delivery system to be transported to and preferentially taken up by a target tissue, and a drug moiety that is covalently bonded to the polymer backbone through a spacer and contains a cleavable group that can be cleaved only by a specific enzyme at the target tissue.

There are a number of controlled release formulations that are developed preferably for oral administration. These include, but are not limited to, osmotic pressure-controlled gastrointestinal delivery systems; hydrodynamic pressure-controlled gastrointestinal delivery systems; membrane permeation-controlled gastrointestinal delivery systems, which include microporous membrane permeation-controlled gastrointestinal delivery devices; gastric fluid-resistant intestine targeted controlled-release gastrointestinal delivery devices; gel diffusion-controlled gastrointestinal delivery systems; and ion-exchange-controlled gastrointestinal delivery systems, which include cationic and anionic drugs. Additional information regarding controlled release drug delivery systems may be found in Yie W. Chien, *Novel Drug Delivery Systems,* 1992 (Marcel Dekker, Inc.). some of these formulations will now be discussed in more detail.

Enteric coatings are applied to tablets to prevent the release of drugs in the stomach either to reduce the risk of unpleasant side effects or to maintain the stability of the drug which might otherwise be subject to degradation of expose to the gastric environment. Most polymers that are used for this purpose are polyacids that function by virtue or the fact that their solubility in aqueous medium is pH-dependent, and they require conditions with a pH higher then normally encountered in the stomach.

One preferable type of oral controlled release structure is enteric coating of a solid or liquid dosage form. Enteric coatings promote the compounds remaining physically incorporated in the dosage form for a specified period when exposed to gastric juice. Yet the enteric coatings are designed to disintegrate in intestinal fluid for ready absorption. Delay of absorption is dependent on the rate of transfer through the gastrointestinal tract, and so the rate of gastric emptying is an important factor. Some investigators have reported that a multiple-unit type dosage form, such as granules, may be superior to a single-unit type. Therefore, in one embodiment, a functional components or active ingredient may be contained in an enterically coated multiple-unit dosage form. In a more preferable embodiment, the active ingredient dosage form is prepared by producing particles having an active ingredient-enteric coating agent solid on an inert core material. These granules can result in prolonged absorption of the drug with good bioavailability.

Typical enteric coating agents include, but are not limited to, hydroxypropylmethylcellulose phthalate, methacryclic acid-methacrylic acid ester copolymer, polyvinyl acetate-phthalate and cellulose acetate phthalate. Akihiko Hasegawa, *Application of solid dispersions of Nifedipine with enteric coating agent to prepare a sustained-release dosage form,* Chem. Pharm. Bull. 33: 1615–1619 (1985). Various enteric coating materials may be selected on the basis of testing to achieve an enteric coated dosage form designed ab initio to have a preferable combination of dissolution time, coating thicknesses and diametral crushing strength. S. C. Porter et al., *The Properties of Enteric Tablet Coatings Made From Polyvinyl Acetate-phthalate and Cellulose acetate Phthalate,* J. Pharm. Pharmacol. 22:42p (1970).

On occasion, the performance of an enteric coating may hinge on its permeability. S. C. Porter et al., *The Permeability of Enteric Coatings and the Dissolution Rates of Coated Tablets,* J. Pharm. Pharmacol. 34: 5–8 (1981). With such oral delivery systems, the component release process may be initiated by diffusion of aqueous fluids across the enteric coating. Investigations have suggested osmotic driven/rupturing effects as important release mechanisms from enteric coated dosage forms. Roland Bodmeier et al., *Mechanical Properties of Dry and Wet Cellulosic and Acrylic Films Prepared from Aqueous Colloidal Polymer Dispersions used in the Coating of Solid Dosage Forms*, Pharmaceutical Research, 11: 882–888 (1994).

The selection of the carrier may have an influence on the dissolution characteristics of the dispersed component in a liquid because the dissolution rate of a component from a surface may be affected by other components in a multiple component mixture. For example, a water-soluble carrier may result in a fast release of the drug from the matrix, or a poorly soluble or insoluble carrier may lead to a slower release of the drug from the matrix. The solubility of the active ingredient may also be increased owing to some interaction with the carriers.

The controlled release properties may be provided by a combination of hydrophilic polymers. In certain cases, a rapid release of the component may be desirable in order to facilitate a fast onset of therapeutic affect. Hence one layer of the tablet may be formulated as an immediate release granulate. By contrast, the second layer of the tablet may release the drug in a controlled manner, preferably through the use of hydrophilic polymers. This controlled release may result from a combination of diffusion and erosion through the hydrophilic polymer matrix.

The food components of the invention can be incorporated into any one of the aforementioned controlled released dosage forms, or other conventional dosage forms. The amount of components contained in each dose can be adjusted, to meet the needs of the individual patient, and the indication. One of skill in the art and reading this disclosure will readily recognize how to adjust the level of component and the release rates in a controlled release formulation, in order to optimize delivery of the component and its bioavailability.

EXEMPLARY USES OF EMBODIMENTS 1 and 3 OF THE PRESENT INVENTION

Embodiments 1 and 3 can be used for the production of improved products including pharmaceuticals and foods of the present invention when used to produce small, uniform particles of a single formulation. The formulation may contain more than one nutrient or active ingredient, either as separate compounds and/or as conjugated compounds. For example, a single formulation may contain carbohydrate and an excipient that provides controlled release of the carbohydrate. In another example, the formulation may contain a nutrient such as a mineral conjugated to an excipient (such as a protein, amino acid, salt, etc.) that provides better absorption of the molecule. In yet another example, the nutrients themselves may be provided in a form that can be better absorbed into the gastrointestinal system, e.g. as "micronutrients"

Formulations to Increase Bioavailability

Bioavailability is defined as the efficiency with which a natural or manufactured source of an element delivers the element to storage or supplies it to metabolically active tissue or to a protein. The methods of the invention can improve bioavailability of ceratin drugs and nutrients by providing them in an improved form for ingestion from a formulation with drugs or food, by providing the main active component (e.g. drugs) with other components that increase the bioavailability of the main active component, or by providing the main active component in a time release formulation.

Certain nutrients, e.g. minerals, can be conjugated to proteins, amino acids, salts, etc. to increase the bioavailability, and these conjugates can be particularized using the methods of the invention. See e.g., Wapnir, *Am J Clin Nutr* 67:1054S-60S (1998). The presence of these conjugates as discrete particles can also increase the bioavailability of the particles, as the bioavailability of many minerals in vivo is limited by their ability to form strongly bound compounds which are not absorbed by the body. By providing discrete conjugates that are absorbed before agglomeration of the nutrient, the bioavailability of a nutrient may be significantly increased.

A number of nutrients display improved absorption in the presence of other food components. For example, absorption of calcium and magnesium can be stimulated by co-ingestion of sugars such as lactulose and oligofructose. Brommage et al., J. Nutr. 123:218&2194 (1993); Delzenne et al., *Life Sci.*, 57:1579–1587 (1995); Ohta et al., *Int. J Vitam. Nutr. Res.* 64:316–323 (1994). The addition of these components in food in an amount that increases mineral absorption but that does not overly affect the flavor or texture of food can be accomplished using the methods of the present invention which are sizing and coating of particles to obtain a desired result.

Infant formulas

Infant formulas are a special food category that must meet the special needs of infants. The present invention can be used to add numerous additives or functional components to infant formulas that would optimize the growth and/or health of infants.

For example, babies fed on commercial formulas do not receive the same immune protection as babies receiving human breast milk. Infant formula of the invention could be enhanced to contain physical and/or chemical immune boosters, such as echinacea extract, or antibodies against certain pathogens that they would normally receive in breast milk. Babies with certain medical needs could also have drugs such as antibiotics added to the formula to prevent or treat infection while allowing ease of administering these drugs to the infants.

In addition, there are no commercially available infant formulas suitable for low birth weight and preterm formulas. Such formulas need to compensate for the increased nutritional needs of premature, low weight, and very low weight infants. The devices and methods of the invention could increase the overall nutritional value of the formulas by providing these nutrients with better bioavailability; or combinations of nutrients not currently available with conventional technology, e.g. due to chemical interactions in the formulation.

EXEMPLARY USES OF EMBODIMENT 2 OF THE PRESENT INVENTION

Embodiment 2 of the device of the present invention provides methods of coating one formulation with another formulation by providing fluids from concentric needles. This allows the production of multi-layered particles (e.g., if separate liquids are delivered in the concentric needles) or hollow particles (e.g., if the innermost fluid is a gas). This methods allows the introduction of a number of components to pharmaceutical or food products, including multi-layered functional components, hollow food and drug additives, and the like, as described in more detail below.

Foods with Coated Functional Particles that Enhance Flavor, Taste and/or Texture The methods of the invention can be used to coat functional components with a substance having a desirable quality for food flavor or texture (e.g.,spices, seasonings, natural flavorings, essential oils, fats, oleoresins, natural extracts, sugar, artificial sweeteners, salt, sour, or bitter flavors or mixtures thereof, etc.) This effectively allows a reduction in the use of the coating substance, and increase in the amount of the desirable component to be coated. Thus, a food product can be made containing a particle that contains a functional component such as fiber, protein, or a desirable compound that positively affects physiology, where the coated particle gives the food the sensation of having additional amounts of the substance that enhances flavor and/or texture.

Recent guidelines from the US Department of Agriculture (USDA) recommend 6–11 servings per day of grain products for overall good health while the National Cancer Institute recommends a daily intake of 20–30 g of fibre per day for cancer risk reduction. The methods of the invention can be used to produce food products having greater fiber content, while still maintaining the texture and taste of their conventional counterparts, by coating fiber particles with a desirable substance that enhances the flavor, texture, etc of the food. For example, the technology of embodiment 2 can be used to coat a fiber particle, e.g., a bran particle, with a second substance, e.g., a fat, oil, or sugar. The coated particles can be produced to mimic the size of a normal particle found in the foods, e.g., a fat-coated bran particle can be produced to mimic the normal size of a fat globule in the food. This will preserve the flavor and/or feel of the food, increase the amount of dietary fiber, and decrease the amount of the substance used to coat the fiber. This may be especially helpful in creating foods that are lower in fat, e.g. foods designed to decrease cardiovascular disease, or foods lower in sugar, such as foods for diabetics, without sacrificing the taste or texture of the food product.

The RDA of protein per day for an adult is 0.8 grams/kg. For many people, and especially people with limited diets such as vegetarians and vegans, it can be difficult not only to consume the needed amount of protein, but also to consume "complete" protein, i.e. all of the essential amino acids. The device of the invention can be used to "coat" proteins and/or specific amino acids in foods to make the foods higher in protein (or in "complete protein"), but with a more desirable taste and/or texture due to the substance that is coating the protein.

Coating of other filler molecules, such as methylcellulose, casein, starch soybean meal, and the like, is also intended to be encompassed in this embodiment of the present invention. The use of such filler compositions, which preferably do not add to the caloric nature of a food, will be apparent to one skilled in the art upon reading the present disclosure. This will also result in a reduction in the substance coating the filler particle in the food products without sacrificing the desirable qualities of that coating substance.

Food with Components Having Food Additive Coatings

The actual amount of a number of food additives may be decreased using the technology of the invention. For example, if the effectiveness of a food additive is due to its surface area, then coating a filler particle with a food additive will allow use of less of the additive overall, while maintaining the effectiveness of the additive. For example, color additives that are added to food products may be modified by coating a filler particle, e.g., methylcellulose, which will allow the creation of a particle that is composed of mostly filler but that has the properties of a larger particle of the color additive. This will allow maintenance of the color of a food or drink product while limiting the actual amount used in the product. In another example, antimicrobial additives may be used to coat a filler particle, such as starch, to provide a molecule with higher surface area of the antimicrobial while reducing the actual amount of antimicrobial used.

Alternatively, the amount of food additive may be decreased by introduction of hollow spheres composed of the additive, for example a hollow sphere composed of a coloring additive. As with coating a filler, the use of hollow spheres will decrease the overall amount of the additive while maintaining the surface area of the additive.

Food additives that may be used to coat a particle include, but are not limited to: Acidifiers, Adjuvants of flavor, alkalies, anti-browning agents, anti-caking agents, antimicrobial agents, antistalling agents, binders, buffers, sequesters and chelators, coating agents, color agents, surfactants, emulsifiers, extenders, flavors, flavor enhancers, maturing agents (i.e. dough conditioners), sweeteners, and the like.

Foods with Time-release Pharmaceutical Particles

Foods having components that are preferably control-released can be coated with any number of compositions that will allow the component to be released at various times or intervals following ingestion. Using excipients as described in the preceding section on controlled release formulations, particles can be produced which have an internal core of a desired drug (either prescription or OTC), and an outer core of the excipient. Alternatively, particles can be produced which have an external core of a desired drug and an excipient coated around an inert core. The thickness of the outer coating may determine the length of time for release, and so the outer coating of the particles can be varied to provide release over a period of time. For example, particles having a core with functional component can be covered by an excipient coat of varying thickness can be introduced into a single food to allow release over a desired time period. In another example, the particles can have a coating of a uniform thickness to provide delivery of a component at a specific time period, e.g. delivery of insulin following ingestion of the food.

Foods with Incompatible Components

Foods having functional components that are incompatible with the other ingredients of the food product may also be coated using the technology of Embodiment 2 to allow addition of the incompatible component to the functional food. One example of this would be the addition of coated particles of lactase to a dairy product such as milk, cheese or ice cream. The lactose can be delivered with these lactose-containing products to aid in the digestion of the product by people afflicted with lactose intolerance. This would preclude the need for additional supplements, and would provide the proper amount of lactase with the lactose-containing product. Another example of the addition of an enzyme incompatible with the food product is the addition of coated amylase particles to certain high-fiber foods such as such as canned beans to aid in digestion. In yet another example of a compound which blocks the uptake of undesirable components (e.g. fats) could be combined with foods containing those undesirable components. Foe example, a drug such as Xenical™ which blocks fat absorption is combined with a high fat food such as hamburger.

The addition of incompatible food components is particularly useful in infant formulas. Lactose is the primary carbohydrate in breast and cow milk. Some infants are deficient in the enzyme, especially premature and lactase-deficient infants. Soy proteins are not as nutritious as milk proteins and calcium is not as easily absorbed from soy formulas as from cow-milk formulas. For infants having such problems, addition of a component containing lactase to break down the lactose would allow the formulas to be based upon cow's milk, but would allow the infants to properly digest the formula Other components that, when added to a food, may cause the food to change in nature of texture can also be added to a food by coating the particle for release during digestion. For example, gelatin has been associated with the promotion of healthy bones and joints. The addition of gelatin into a beverage, however, changes the nature of the beverage because it begins to gel. The gelatin may be coated and added to the beverage to provide the benefits of the gelatin while maintaining the fluid nature of the beverage.

Foods Fortified with Components that Alter Taste

The device of the invention can also be used to introduce components to food while masking negative effects of the component on the food. For example, a number of functional components and additives, e.g., minerals such as iron, may alter the taste of a food product. Where it is desirable to introduce a component that affects the flavor of a food, the flavor of the component may be masked by a coating that has either a neutral flavor or a flavor that actively enhances the food product. Some research has shown that omega-3 fatty acids, found in fish such as salmon and mackerel as well as in soybean and canola oil, lower both LDL-cholesterol and triglyceride levels in the blood. Similarly, garlic extract has been touted as reducing blood cholesterol levels. Since both of these components strongly (and generally negatively) influence the flavor of a food, coating these components can allow them to be added to a wide variety of foods, e.g., energy bars or baked goods.

Packaging Materials

The packing material of food e.g. cookies can be impregnated with particles which encapsulate a gas which includes a desired smell e.g. fresh baked cookie smell. When the package is torn open the particles are opened releasing the desired smell. The encapsulated food smells could also be used in product advertising.

Controlled Release Formulations

Any food, food additives, drug, nutritional or other desired material can be formulated using different aspects of the invention to obtain a desired controlled release profile. One means of obtaining a controlled release profile is to make a formulation which includes particle size increasing from a first known size to a second larger know size, etc. If the size of each group (e.g. 2–10) group of particles has a known well defined size with a narrow size distribution in that group then the release rate of materials from that group of particles can be determined. The smaller the particles in a group, the faster the rate of release. Thus, by producing a formulation of several groups of particles of different sizes, the rate of release of the formulation as a whole can be controlled. This can be done, for example, to control the rate in which sugar in a food is released to a diabetic patient to aid in controlling glucose levels. This could be done with a drug to (a) quickly obtain a therapeutic level with a first quick release drug, and (b) obtained a constant level of the drug thereafter over a given period of time by balancing the rate of release of subsequent groups against the rate at which the drug is cleared from the body.

Although the use of groups of particles of different sizes in a formulation may obtain the desired results, it may not be possible to obtain the desired results with all materials. For example, some materials will dissolve too quickly to obtain the desired controlled release result only by using particles of different sizes in different groups.

In such a situation, the desired controlled release results can be obtained by coating particles. In one embodiment, the core particles are all the same size as obtainable via the present invention. The formulation comprises a plurality of groups of particles wherein all the particles of a given group have a coating which is substantial the same size and thickness. However, the coating thickness differs from one group to another.

A first group may include a very thin coating or no coating at all. Each subsequence group will comprise particles with thicker and thinner coatings. The rate of release of a drug from particles in any group can be determined. By knowing the rate of release of each group a desired formulation can be produced with the desired rate of release.

A preferred formulation will quickly release enough drug to obtain a therapeutic level of drug in the patient, e.g. in blood. Thereafter, that level of drug will be maintained in a desired therapeutic range over a desired period of time, e.g. hours, days, weeks, months, etc.

Figure 3B:
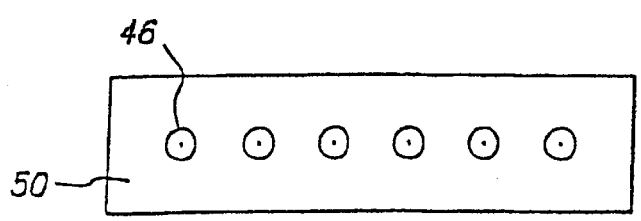
FIGS. 3a–3c is a schematic views of yet another embodiment showing a wedge-shaped planar source of formulation.
Figure 3A:
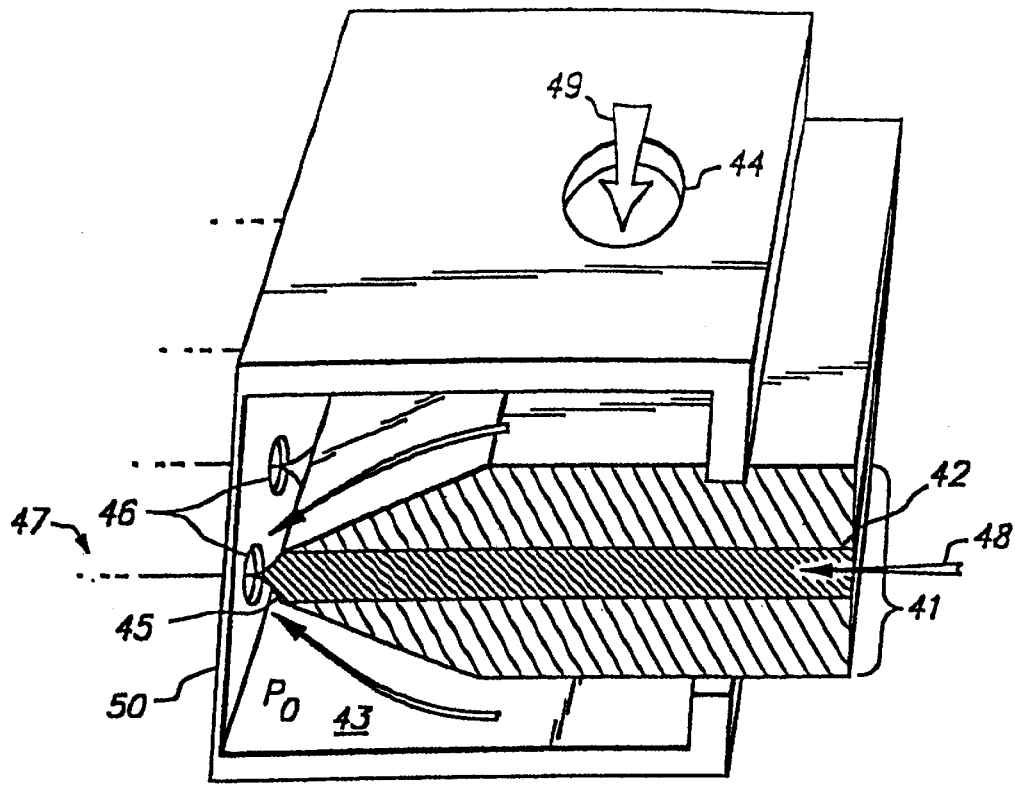
Figure 3C:
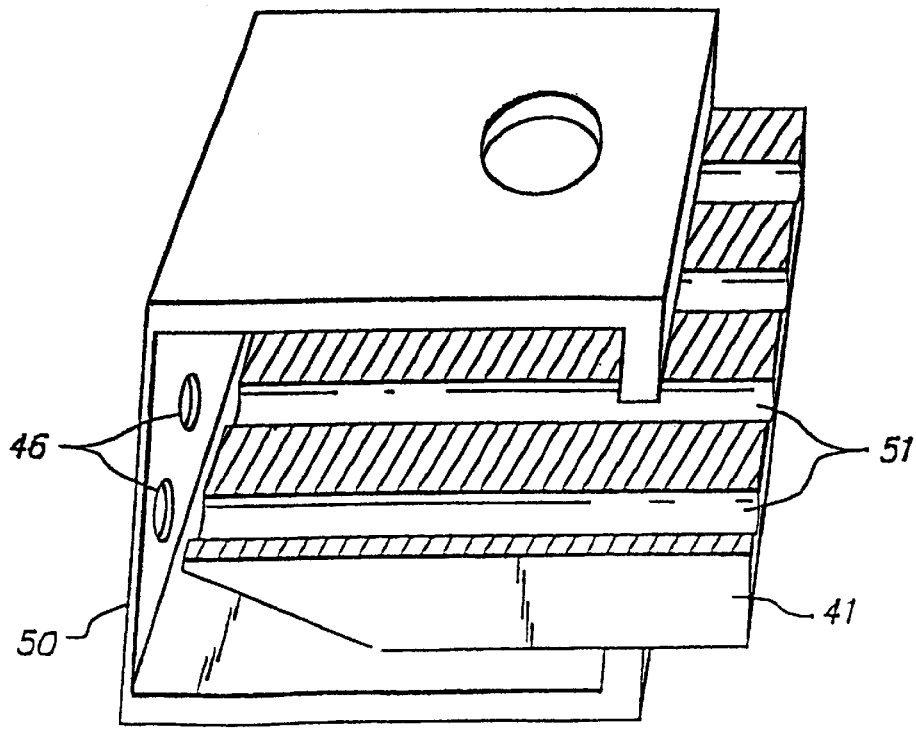

The embodiments of FIGS. 2 and 3 can be combined and used to more rapidly produce controlled release formulations on a commercial scale. In FIG. 3C there are a plurality of semicircular grooves 51 which form a plurality of extrusion tubes which are equivalent to the feeding tube 1 of FIG. 1 or tube 21 of FIG. 2. Each of the tubes formed by the two parts of the channels or grooves 51 can have an inner feeding tube inserted therein such as the inner tube 31 of FIG. 2. The inner feeding tube (not shown in FIG. 3) is used to supply a liquid food or drug and the outer tube formed using the channels 51 are used to supply the coating material, e.g. a polymer material generally used in connection with a controlled release formulations such as methylcellulose. The device is modified so that different groups of tubes formed by the channels 51 have different diameters. For example, a first group of channels 51 form tubes with a diameter of 10 microns and each have an inner feeding tube with a diameter of 5 microns. The inner feeding tube supplies the active component such as a pharmaceutical active drug. The inner tubes may have different diameters but preferably all have the same diameter. A second group of channels 51 form tubes with a diameter of 11 microns and each has an inner feeding tube with a diameter of 5 microns. Each successive group of channels 51 has a larger diameter but includes an inner feeding tube having the same diameter. When the device is operated, active material (e.g. drug or food) is supplied to the inner feeding tube and a coating material (e.g. an inactive, non-toxic polymer) is supplied to the outer groups of channels 51. The operation results in forming groups of particles wherein all groups have an inner core sphere of the same size but where the coating of each group of particles is larger than the coating of the previous group. Thus, a formulation of controlled release particles of different groups with different rates of release can be simultaneously produced.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. A method for producing a food product, comprising the steps of:

forcing a liquid food through a channel of a feeding source in a manner which causes the liquid to be expelled from an exit opening;

forcing a gas through a pressure chamber in a manner which causes the gas to exit the pressure chamber from an exit orifice down stream of a flow path of the liquid expelled from the exit opening of the feeding source;

wherein a stable first liquid-gas interface is maintained and the liquid forms a stable jet focused on the exit orifice of the pressure chamber by the gas; and wherein said jet dissociates into particles after expulsion from the exit opening, said particles having the same diameter with a deviation of about ±3% to about ±30%.

2. The method of claim 1, wherein the feeding source is a cylindrical channel and the liquid is expelled from an exit opening having a diameter in the range of from about 0.002 to about 2 mm and wherein the opening in the pressure chamber has a diameter in the range of about 0.002 to about 2 mm and is positioned directly down stream of a flow path of the exit opening of the channel.

3. The method of claim 1, wherein the exit opening has a diameter in the range of from about 100 nm to about 0.1 mm, and wherein the exit opening of the feeding source is separated by a distance of from about 0.002 mm to about 2 mm from the exit opening in the pressure chamber.

4. The method of claim 1, wherein the exit opening has a diameter of from about 0.002 micron to about 100 microns.

5. The method of claim 4, further comprising:

dispersing the particles in a food.

6. The method of claim 5, wherein the particles are uniformly dispersed in the food.

7. A method for producing encapsulated particles, comprising the steps of:

forcing a first liquid through a channel of a first feeding source in a manner which causes the first liquid to be expelled from an exit opening;

forcing a second liquid through a channel of a second feeding source in a manner which causes the second liquid to be expelled from an exit opening, wherein said second liquid surrounds said first liquid as said first liquid moves from the first feeding source; and forcing a gas through a pressure chamber in a manner which causes the gas to exit the pressure chamber from an exit orifice down stream of a flow path of the first and second liquids expelled from the exit opening of the feeding sources;

wherein a stable liquid-gas interface is maintained between the second liquid and the gas, and the first and second liquids are immiscible and form a stable capillary jet focused on the exit orifice of the pressure chamber by the gas.

8. The method of claim 7, wherein the first liquid is a food and the second liquid is a polymer material which encapsulates particles which form when the jet leave the pressure chamber.

9. The method of claim 7, wherein the first liquid is a food with high nutritional value and offensive taste and the second liquid is a polymer which encapsulates particles which form when the jet leave the pressure chamber.

10. The method of claim 7, wherein the first liquid is a pharmaceutically active drug and the second layer is a polymer which encapsulates particles which form when the jet leave the pressure chamber.

* * * * *